United States Patent
Ebner et al.

(10) Patent No.: US 6,603,039 B1
(45) Date of Patent: Aug. 5, 2003

(54) DEEPLY REDUCED OXIDATION CATALYST AND ITS USE FOR CATALYZING LIQUID PHASE OXIDATION REACTIONS

(75) Inventors: Jerry R. Ebner, St. Charles, MO (US); Mark A. Leiber, St. Peters, MO (US); Kam-To Wan, Manchester, MO (US); Peter E. Rogers, Des Peres, MO (US); Jingyue Liu, Chesterfield, MO (US); Anthony Woods, Cambridge (GB)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/408,296

(22) Filed: Sep. 29, 1999

Related U.S. Application Data

(62) Division of application No. 09/248,655, filed on Feb. 11, 1999, now Pat. No. 6,417,133.
(60) Provisional application No. 60/075,988, filed on Feb. 25, 1998.

(51) Int. Cl.$^7$ .................................................. C07F 9/38
(52) U.S. Cl. ........................ 562/17; 502/174; 502/180; 502/182; 502/183; 502/184
(58) Field of Search ........................ 562/17; 502/174, 502/180, 182, 183, 184

(56) References Cited

U.S. PATENT DOCUMENTS

| | | | |
|---|---|---|---|
| 3,340,097 A | 9/1967 | Hess et al. ................. 136/120 |
| 3,799,758 A | 3/1974 | Franz ............................ 71/86 |
| 3,835,000 A | 9/1974 | Frazier et al. ................ 204/78 |
| 3,927,080 A | 12/1975 | Gaetner ................... 260/502.5 |
| 3,950,402 A | 4/1976 | Franz ..................... 260/502.5 |
| 3,954,848 A | 5/1976 | Franz ..................... 260/502.5 |
| 3,956,370 A | 5/1976 | Parry et al. ............. 260/502.5 |
| 3,969,398 A | 7/1976 | Hershman ............... 260/502.5 |
| 4,026,950 A | 5/1977 | Le Ludec ............... 260/600 R |
| 4,147,719 A | 4/1979 | Franz .................... 260/501.12 |
| 4,186,110 A | 1/1980 | Jalan et al. |
| 4,190,605 A | 2/1980 | Muench et al. ......... 260/600 R |
| 4,264,776 A | 4/1981 | Hershman et al. .......... 564/384 |
| 4,415,479 A | 11/1983 | Puskas et al. ................. 502/85 |
| 4,507,250 A | 3/1985 | Bakel ................... 260/502.5 F |
| 4,525,294 A | 6/1985 | Sartori et al. ............... 252/182 |
| 4,582,650 A | 4/1986 | Felthouse ............. 260/502.5 F |
| 4,624,937 A | 11/1986 | Chou ........................ 502/180 |
| 4,654,429 A | 3/1987 | Balthazor et al. ........... 558/145 |
| 4,696,772 A | 9/1987 | Chou ................... 260/502.5 F |
| 4,775,498 A | 10/1988 | Gentilcore ............ 260/502.5 F |
| 4,810,426 A | 3/1989 | Fields, Jr. et al. .... 260/502.5 F |
| 4,851,131 A | 7/1989 | Grabiak et al. .............. 210/763 |
| 4,921,991 A | 5/1990 | Lacroix ...................... 558/135 |
| 4,978,649 A | 12/1990 | Surovikin et al. .......... 502/416 |
| 5,023,369 A | 6/1991 | Fields, Jr. |
| 5,077,431 A | 12/1991 | Fields, Jr. |
| 5,087,740 A | 2/1992 | Smith ......................... 562/17 |
| 5,091,561 A | 2/1992 | Riley et al. |
| 5,095,140 A | 3/1992 | Fields, Jr. |
| 5,179,228 A | 1/1993 | Martin Ramon et al. ..... 562/17 |
| 5,292,936 A | 3/1994 | Franczyk ................... 562/526 |
| 5,356,849 A | 10/1994 | Matviya et al. ............. 502/180 |
| 5,367,112 A | 11/1994 | Franczyk ................... 562/526 |
| 5,410,085 A | 4/1995 | Birkenstock et al. ........ 564/417 |
| 5,500,485 A | 3/1996 | Hodgkinson .................. 562/18 |
| 5,585,083 A | 12/1996 | Kielin et al. ............. 423/245.3 |
| 5,602,276 A | 2/1997 | Stern et al. ................... 562/16 |
| 5,606,107 A | 2/1997 | Smith ........................... 562/17 |
| 5,627,125 A | 5/1997 | Ebner et al. ................. 502/331 |
| 5,658,839 A | 8/1997 | de Agudelo et al. .......... 502/74 |
| 5,688,994 A | 11/1997 | Baysdon et al. .............. 562/17 |
| 5,876,867 A | 3/1999 | Itoh et al. |
| 5,882,619 A | 3/1999 | Heineke et al. |
| 6,005,140 A | 12/1999 | Morgenstern et al. ........ 562/17 |

FOREIGN PATENT DOCUMENTS

| | | |
|---|---|---|
| AU | 58285/80 A | 11/1980 |
| EP | 0019445 B2 | 11/1980 |
| EP | 0019445 B1 | 11/1980 |
| EP | 0 055 695 | 7/1982 |
| EP | 0 098 034 A2 | 1/1984 |
| EP | 0 162 035 A2 | 11/1985 |
| EP | 0 408 528 A1 | 1/1991 |
| EP | 0 595 124 A1 | 5/1994 |
| EP | 0 680 948 A1 | 11/1995 |
| EP | 0 081 978 A1 | 10/1997 |
| GB | 1 601 715 | 11/1981 |
| WO | WO/00/01707 | 1/2000 |

OTHER PUBLICATIONS

Jul. 9, 1999 PCT Search Report in Application PCT/US99/03402, Filed Feb. 17, 1999 (which corresponds to this application).

Andrew, M.R. et al., "The Characterization of Pt/Sn Catalyst For The Electrochemical Oxidation of Methanol", *Journal Of Applied Electrochemistry*, 6, pp. 99–106, 1976.

Aricò, A.S. et al., "Methanol Oxidation On Carbon–Supported Pt–Sn Electrodes In Silicotungstic Acid", *Electrochimica Acta.*, vol. 39, No. 5, pp. 691–700, 1994.

(List continued on next page.)

*Primary Examiner*—Kathleen K. Fonda
*Assistant Examiner*—Leigh C. Maier
(74) *Attorney, Agent, or Firm*—Senniger, Powers, Leavitt & Roedel; Joseph A. Schaper

(57) ABSTRACT

This invention relates to an improved catalyst, comprising a carbon support having a noble metal at its surface, for use in catalyzing liquid phase oxidation reactions, especially in an acidic oxidative environment and in the presence of solvents, reactants, intermediates, or products which solubilize noble metals; a process for the preparation of the improved catalyst; a liquid phase oxidation process using such a catalyst wherein the catalyst exhibits improved resistance to noble metal leaching, particularly in acidic oxidative environments and in the presence of solvents, reactants, intermediates, or products which solubilize noble metals; and a liquid phase oxidation process in which N-(phosphonomethyl)iminodiacetic acid (i.e., "PMIDA") or a salt thereof is oxidized to form N-(phosphonomethyl) glycine (i.e., "glyphosate") or a salt thereof using such a catalyst wherein the oxidation of the formaldehyde and formic acid by-products into carbon dioxide and water is increased.

104 Claims, 2 Drawing Sheets

OTHER PUBLICATIONS

Balakrishnan, K. et al., "A Chemisorption And XPS Study Of Bimetallic Pt–Sn/Al$_2$O$_3$ Catalysts", *Journal of Catalysis* 127, pp. 287–306, 1991.

Burch, R., "The Oxidation State Of Tin And The Interaction Between Platinum And Tin", *Journal of Catalysis*, pp. 348–359, 1981.

Cameron, D.S. et al., "Carbons As Supports For Precious Metal Catalysts", *Catalysis Today*, vol. 7, pp. 113–137, 1990.

Campbell, S. et al., "Effect Of Bi And Sn Adatoms On Formic Acid And Methanol Oxidation At Well Defined Platinum Surfaces", *Journal of Chemical Society*, Faraday Trans., vol. 88, No. 6, pp. 833–841, 1992.

Cathro, K.J., "The Oxidation Of Water–Soluble Organic Fuels Using Platinum–Tin Catalysts", *J. Electrochem. Soc.: Electrochemical Technology*, vol. 116, No. 11, pp. 1608–1611, 1969.

Coloma, F. et al., "Heat–Treated Carbon Blacks As Supports For Platinum Catalysts", *Journal of Catalysis* 154, pp. 299–305, 1995.

Coloma, F. et al., "Preparation Of Platinum Supported On Pregraphitized Carbon Blacks", *Langmuir*, 10, pp. 750–755, 1994.

Dubinin, M.M., "Microporous Structures Of Carbonaceous Adsorbents", *Carbon*, vol. 20, No. 3, pp. 195–200, 1982.

Franklin, T. et al., "The Effect Of Anionic Poisons On the Catalytic Oxidation Of Formaldehyde On Platinum", *Journal of Catalysis* 42, pp. 360–366, 1976.

Gallezot, P. et al., "Catalytic Oxidations With Air For Clean And Selective Transformations Of Polyols", *Catalysis Of Organic Reactions*, pp. 331–340, (Scaros et al., eds. Marcel Dekker, Inc., New York, NY, 1994).

Gökağac, G. et al., "Characterisation Of Carbon–Supported Pt–Sn Bimetallic Catalysts for The Electrochemical Oxidation Of Methanol", *Journal of Chemical. Society*, Faraday Trans., vol. 89, No. 1, pp. 151–157, 1993.

Kim, T.K. et al., "Preparation Of Carbon–Supported Platinum Catalysts: Adsorption Mechanism of Anionic Platinum Precursor Onto Carbon Support", *Carbon*, vol. 30, No. 3, pp. 467–475, 1992.

Kimura, H. et al., "Palladium Based Multi–Component Catalytic Systems For the Alcohol To Carboxylate Oxidation Reaction", *Applied Catalysis A: General*, vol. 95, pp. 143–169, 1993.

Kimura, H., "Selective Oxidation Of Glycerol On A Platinum–bismuth Catalyst By Using a Fixed Bed Reactor", *Applied Catalysis A: General*, vol. 105, pp. 147–158, 1993.

Luk'yanova, Z.V. et al., "Determination Of the Surface Area Of Platinum In Adsorption Catalysts From The Amount Of 'Soluble' Platinum", *Russian Journal of Physical Chemistry*, vol. 53, No. 2, pp. 225–227, 1979.

Maier, L., "Organic Phosphorus Compounds 95. A Simple Method For The Preparation Of N–Dihydroxyphosphonylmethyl–Glycine (Glyphosate)", *Phosphorus, Sulfur, and Silicon*, vol. 61, pp. 65–67, 1991.

Mallat, T. et al., "Preparation Of Promoted Platinum Catalysts Of Designed Geometry And The Role Of Promoters In The Liquid–Phase Oxidation of 1–Methoxy–2–Propanol", *Journal Of Catalysis* 142, pp. 237–253, 1993.

Margitfalvi, J. et al., "Supported Bimetallic Catalysts Prepared By Controlled Surface Reactions", ch. 11, pp. 373–409, 1992.

Merlen, E. et al., "Characterization Of Bimetallic Pt–Sn/Al$_2$O$_3$ Catalysts: Relationship Between Particle Size And Structure", *Journal of Catalysis* 159, pp. 178–188, 1996.

Prado–Burguette, C. et al., "Effect of Caarbon Support And Mean Pt Particle Size On Hydrogen Chemisorption By Carbon–Supported Pt Catalysts", *Journal of Catalysis 128*, pp. 397–404, 1991.

Prado–Burgette, C. et al., "The Effect Of Oxygen Surface Groups Of The Support On Platinum Dispersion In Pt/Carbon Catalysts", *Journal of Catalysis* 115, pp. 98–106, 1989.

Riley, D. et al., "Vanadium (IV, V) Salts As Homogeneous Catalysts For The Oxgen Oxidation of N–(Phosphonomethyl)Iminodiacetic Acid To N–(Phosphonomethyl)Glycine", *Inorg. Chem*, vol. 30, pp. 4191–4197, 1991.

Riley, D. et al.,"Homogeneous Catalysts For Selective Molecular Oxygen Drive Oxidative Decarboxylations", *J. Am. Chem. Soc.*, vol. 113, pp. 3371–3378, 1991.

Rodríguez–Reinoso, F. et al., "Platinum Catalysts Supported On Activated Carbons", *Journal Of Catalysis* 99, pp. 171–183, 1986.

Shekhobalova, V.I., "Effect Of Small Additions Of Kl On The Properties Of Pt Adsorption Catalysts", *Russian Journal Of Physical Chemistry*, vol. 58, No. 11, pp. 1759–1760, 1984.

Shekhobalova, V.I. et al., "Deactivation Mechanism Of Platinum Catalysts During The Liquid–Phase Decompositoin Of Hydrogen Peroxide", *Russian Journal Of Physical Chemistry*, vol. 53, No. 9, pp. 1308–1309, 1979.

Shekhobalova, V.I. et al., "Relationship Between The Shape Of the Kinetic Curves For the Catalytic Decomposition Of Hydrogen Peroxide And The Amount of 'Soluble' Metal In The Catalyst", *Russian Journal Of Physical Chemistry*, vol. 53, No. 6, pp. 917–918, 1979.

Van Dam, H.E. et al., "Preparation Of Platinum On Activate Carbon", *Journal of Catalysis 131*, pp. 335–349, 1991.

Vértes, Cs. et al., "Mössbauer Spectroscopy Studies Of Sn–Pt/Al$_2$O$_3$ Catalysts Prepared By Controlled Surface Reactions", *Applied Catalysis*, vol. 68, pp. 149–159, 1991.

Watanabe, M. et al., "Electrocatalysis By Ad–Atoms: Part XIII. Preparation Of Ad–electrodes With Tin Ad–Atoms For Methanol, Formaldehyde And Formic Acid Fuel Cells", *J. Electroanal. Chem.*, vol. 191, pp. 367–375, 1985.

*CRC Handbook Of Chemistry And Physics 79$^{th}$ Edition*, pp. 10–176, (Lide, D.R., ed., CRC Press, Boca Raton, FL, 1998–1999).

"Preparation And Characterization Of Metal And Alloy Catalysts", *Studies In Surface Science And Catalysis: Catalysis By Metal And Alloys*, ch.7, vol. 95, pp. 299–391, (Delman, B., et al., eds, Elscvier Science B.V., Amsterdam, Netherlands).

Kim, Kyong Tae et al., "Surface And Catalytic Properties Of Iron–Platinum/Carbon Electrocatalysts For Cathodic Oxygen Reduction In PAFC", J. Electrochem. Soc., vol. 140, No. 1, pp. 31–36, 1993.

FIG·1

DEEPLY REDUCED OXIDATION CATALYST AND ITS USE FOR CATALYZING LIQUID PHASE OXIDATION REACTIONS

This application is a divisional of U.S. patent application Ser. No. 09/248,655, filed Feb. 11, 1999, now U.S. Pat. No. 6,417,133, which claims priority from U.S. Provisional Patent Application Ser. No. 60/075,988, filed Feb. 25, 1998. U.S. patent application Ser. No, 09/248,655 and U.S. Provisional Patent Application Serial No. 60/075,988 are incorporated herein by reference.

BACKGROUND OF THE INVENTION

This invention generally relates to an improved oxidation catalyst and its use for catalyzing liquid phase oxidation reactions, especially in acidic oxidative environments and in the presence of reactants, intermediates, products, or solvents which solubilize noble metals. In a preferred embodiment, the present invention relates to an improved oxidation catalyst and a process in which the catalyst is used to convert N-(phosphonomethyl)iminodiacetic acid or a salt thereof into N-(phosphonomethyl)glycine or a salt thereof.

N-(phosphonomethyl)glycine (known in the agricultural chemical industry as "glyphosate") is described in Franz, U.S. Pat. No. 3,799,758. N-(phosphonomethyl)glycine and its salts are conveniently applied as a post-emergent herbicide in an aqueous formulation. It is a highly effective and commercially important broad-spectrum herbicide useful in killing or controlling the growth of a wide variety of plants, including germinating seeds, emerging seedlings, maturing and established woody and herbaceous vegetation, and aquatic plants.

Various methods for making N-(phosphonomethyl)glycine are known in the art. Franz (U.S. Pat. No. 3,950,402) teaches that N-(phosphonomethyl)glycine may be prepared by the liquid phase oxidative cleavage of N-(phosphonomethyl)iminodiacetic acid (sometimes referred to as "PMIDA") with oxygen in the presence of a catalyst comprising a noble metal deposited on the surface of an activated carbon support:

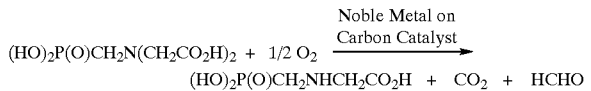

$(HO)_2P(O)CH_2N(CH_2CO_2H)_2 + 1/2\ O_2 \xrightarrow{\text{Noble Metal on Carbon Catalyst}}$
$(HO)_2P(O)CH_2NHCH_2CO_2H + CO_2 + HCHO$ Other by-products also may form, such as formic acid, which is formed by the oxidation of the formaldehyde by-product; and aminomethylphosphonic acid ("AMPA"), which is formed by the oxidation of N-(phosphonomethyl)glycine. Even though the Franz method produces an acceptable yield and purity of N-(phosphonomethyl)glycine, high losses of the costly noble metal into the reaction solution (i.e., "leaching") result because under the oxidation conditions of the reaction, some of the noble metal is oxidized into a more soluble form and both PMIDA and N-(phosphonomethyl)glycine act as ligands which solubilize the noble metal.

In U.S. Pat. No. 3,969,398, Hershman teaches that activated carbon alone, without the presence of a noble metal, may be used to effect the oxidative cleavage of PMIDA to form N-(phosphonomethyl)glycine. In U.S. Pat. No. 4,624,937, Chou further teaches that the activity of the carbon catalyst taught by Hershman may be increased by removing the oxides from the surface of the carbon catalyst before using it in the oxidation reaction. See also, U.S. Pat. No. 4,696,772, which provides a separate discussion by Chou regarding increasing the activity of the carbon catalyst by removing oxides from the surface of the carbon catalyst. Although these processes obviously do not suffer from noble metal leaching, they do tend to produce greater concentrations of formaldehyde by-product when used to effect the oxidative cleavage of N-phosphonomethyliminodiacetic acid. This formaldehyde by-product is undesirable because it reacts with N-(phosphonomethyl)glycine to produce unwanted by-products (mainly N-methyl-N-(phosphonomethyl)glycine, sometimes referred to as "NMG") which reduce the N-(phosphonomethyl)glycine yield. In addition, the formaldehyde by-product itself is undesirable because of its potential toxicity. See Smith, U.S. Pat. No. 5,606,107.

Optimally, therefore, it has been suggested that the formaldehyde be simultaneously oxidized to carbon dioxide and water as the PMIDA is oxidized to N-(phosphonomethyl)glycine in a single reactor, thus giving the following reaction:

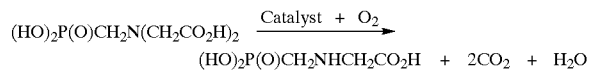

$(HO)_2P(O)CH_2N(CH_2CO_2H)_2 \xrightarrow{\text{Catalyst} + O_2}$
$(HO)_2P(O)CH_2NHCH_2CO_2H + 2CO_2 + H_2O$ As the above teachings suggest, such a process requires the presence of both carbon (which primarily effects the oxidation of PMIDA to form N-(phosphonomethyl)glycine and formaldehyde) and a noble metal (which primarily effects the oxidation of formaldehyde to form carbon dioxide and water). Previous attempts to develop a stable catalyst for such an oxidation process, however, have not been entirely satisfactory.

Like Franz, Ramon et al. (U.S. Pat. No. 5,179,228) teach using a noble metal deposited on the surface of a carbon support. To reduce the problem of leaching (which Ramon et al. report to be as great as 30% noble metal loss per cycle), however, Ramon et al. teach flushing the reaction mixture with nitrogen under pressure after the oxidation reaction is completed to cause re-deposition of the noble metal onto the surface of the carbon support. According to Ramon et al., nitrogen flushing reduces the noble metal loss to less than 1%. Still, the amount of noble metal loss incurred with this method is unacceptable. In addition, re-depositing the noble metal can lead to loss of noble metal surface area which, in turn, decreases the activity of the catalyst.

Using a different approach, Felthouse (U.S. Pat. No. 4,582,650) teaches using two catalysts: (i) an activated carbon to effect the oxidation of PMIDA into N-(phosphonomethyl)glycine, and (ii) a co-catalyst to concurrently effect the oxidation of formaldehyde into carbon dioxide and water. The co-catalyst consists of an aluminosilicate support having a noble metal located within its pores. The pores are sized to exclude N-(phosphonomethyl)glycine and thereby prevent the noble metal of the co-catalyst from being poisoned by N-(phosphonomethyl)glycine. According to Felthouse, use of these two catalysts together allows for the simultaneous oxidation of PMIDA to N-(phosphonomethyl)glycine and of formaldehyde to carbon dioxide and water. This approach, however, suffers from several disadvantages: (1) it is difficult to recover the costly noble metal from the aluminosilicate support for re-use; (2) it is difficult to design the two catalysts so that the rates between them are matched; and (3) the carbon support, which has no noble metal deposited on its surface, tends to deactivate at a rate which can exceed 10% per cycle.

Thus, a need exists for an improved, multi-reaction catalyst and reaction process which oxidizes PMIDA to N-

(phosphonomethyl)glycine while simultaneously exhibiting resistance to noble metal leaching and increased oxidation of formaldehyde into carbon dioxide and water (i.e., increased formaldehyde activity).

SUMMARY OF THE INVENTION

This invention provides for an improved catalyst for use in catalyzing liquid phase oxidation reactions, especially in an acidic oxidative environment and in the presence of solvents, reactants, intermediates, or products which solubilize noble metals; a process for the preparation of the improved catalyst; a liquid phase oxidation process using such a catalyst wherein the catalyst exhibits improved resistance to noble metal leaching, particularly in acidic oxidative environments and in the presence of solvents, reactants, intermediates, or products which solubilize noble metals; and a liquid phase oxidation process in which PMIDA or a salt thereof is oxidized to form N-(phosphonomethyl)glycine or a salt thereof using such a catalyst wherein the oxidation of the formaldehyde by-product into carbon dioxide and water is increased.

Briefly, therefore, the present invention is directed to a process for oxidizing a reagent in a mixture (typically a solution or a slurry, and most typically a solution), wherein the mixture has the ability to solubilize a noble metal. This process comprises contacting the mixture with an oxidation catalyst in the presence of oxygen. In one embodiment, the catalyst comprises a carbon support having a noble metal at its surface. The catalyst is characterized as yielding no more than about 1.2 mmole of carbon monoxide per gram of catalyst when a dry sample of the catalyst in a helium atmosphere is heated from about 20 to about 900° C. at a rate of about 10° C. per minute, and then at about 900° C. for about 30 minutes.

In another embodiment directed to the process for oxidizing a reagent in a mixture which can solubilize a noble metal, the catalyst comprises a carbon support having a noble metal and a promoter at a surface of the carbon support. In addition, the catalyst is characterized as yielding no more than about 1.2 mmole of carbon monoxide per gram of catalyst when a dry sample of the catalyst, after being heated at a temperature of about 500° C. for about 1 hour in a hydrogen atmosphere and before being exposed to an oxidant following the heating in the hydrogen atmosphere, is heated in a helium atmosphere from about 20 to about 900° C. at a rate of about 10° C. per minute, and then at about 900° C. for about 30 minutes.

In another embodiment directed to the process for oxidizing a reagent in a mixture which can solubilize a noble metal, the catalyst comprises a carbon support having a noble metal, carbon, and oxygen at a surface of the carbon support. The ratio of carbon atoms to oxygen atoms at the surface is at least about 20:1 as measured by x-ray photoelectron spectroscopy.

In another embodiment directed to the process for oxidizing a reagent in a mixture which can solubilize a noble metal, the catalyst comprises a carbon support having a noble metal, a promoter, carbon, and oxygen at a surface of the carbon support. The catalyst is characterized as having a ratio of carbon atoms to oxygen atoms at the surface which is at least about 20:1 as measured by x-ray photoelectron spectroscopy after the catalyst is heated at a temperature of about 500° C. for about 1 hour in a hydrogen atmosphere and before the catalyst is exposed to an oxidant following the heating in the hydrogen atmosphere.

In another embodiment directed to the process for oxidizing a reagent in a mixture which can solubilize a noble metal, the catalyst comprises a carbon support having a noble metal at a surface of the carbon support. In addition, the support comprises a surface layer having a thickness of about 50 Å as measured inwardly from the surface and comprising oxygen and carbon. The ratio of carbon atoms to oxygen atoms in the surface layer is at least about 20:1 as measured by x-ray photoelectron spectroscopy.

In another embodiment directed to the process for oxidizing a reagent in a mixture which can solubilize a noble metal, the catalyst comprises a carbon support having: (a) a noble metal and a promoter at a surface of the carbon support; and (b) a surface layer having a thickness of about 50 Å as measured inwardly from the surface and comprising carbon and oxygen. The catalyst is characterized as having a ratio of carbon atoms to oxygen atoms in the surface layer of at least about 20:1 as measured by x-ray photoelectron spectroscopy after the catalyst is heated at a temperature of about 500° C. for about 1 hour in a hydrogen atmosphere and before the catalyst is exposed to an oxidant following the heating in the hydrogen atmosphere.

In another embodiment directed to the process for oxidizing a reagent in a mixture which can solubilize a noble metal, the catalyst is prepared by a process comprising depositing a noble metal at a surface of a carbon support, and then heating the surface at a temperature of at least about 400° C.

In another embodiment directed to the process for oxidizing a reagent in a mixture which can solubilize a noble metal, the catalyst is prepared by a process comprising depositing a noble metal at a surface of a carbon support, and then exposing the surface to a reducing environment. In this embodiment, before the noble metal deposition, the carbon support has carbon and oxygen at the surface of the carbon support in amounts such that the ratio of carbon atoms to oxygen atoms at the surface is at least 20:1 as measured by x-ray photoelectron spectroscopy.

Other features of this invention will be in part apparent and in part pointed out hereinafter.

DETAILED DESCRIPTION OF THE PREFERRED EMBODIMENTS

A. The Oxidation Catalyst

Figure 1:
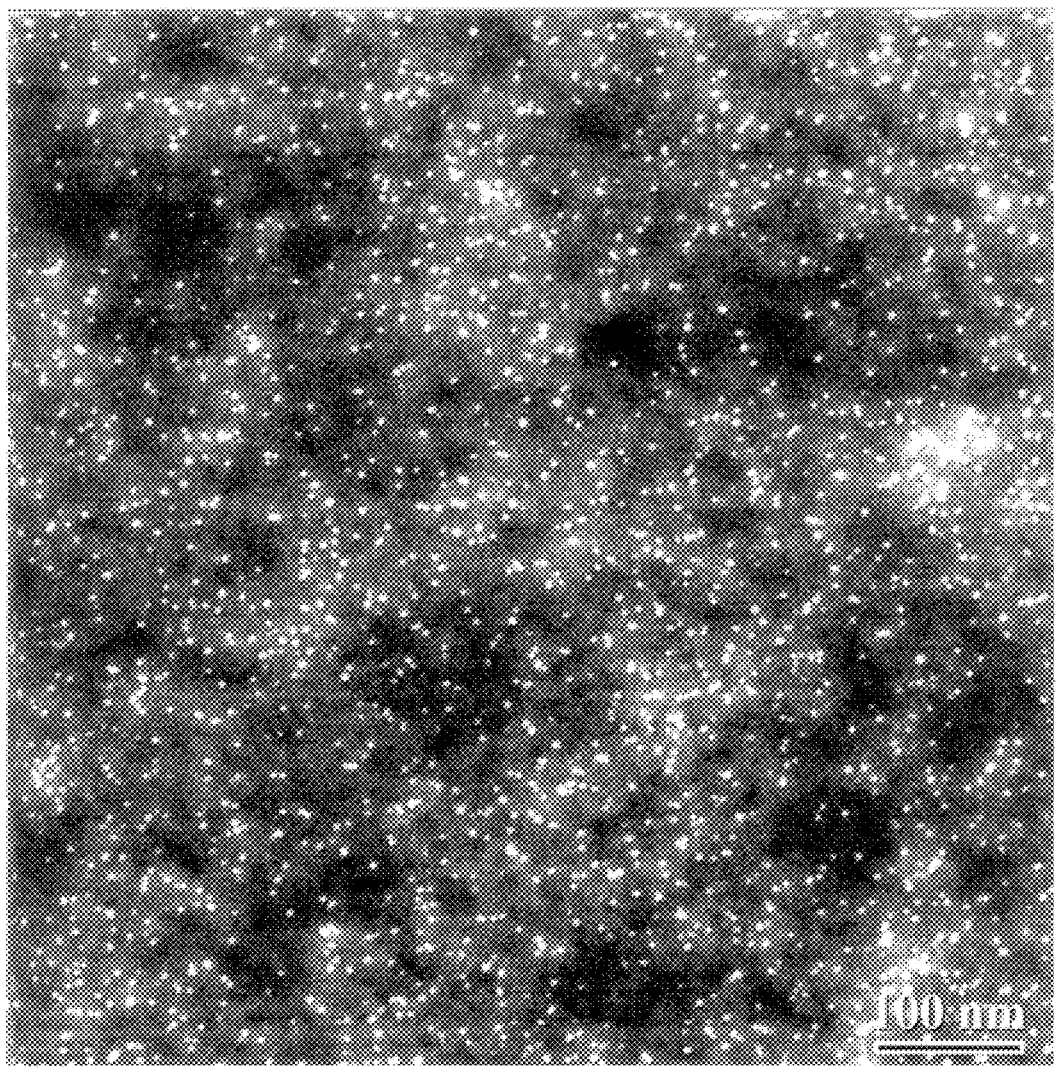
FIG. 1 is a TEM image of an oxidation catalyst comprising a carbon support having platinum alloyed with iron at the surface of the carbon support.

The catalyst of the present invention may be used to catalyze liquid phase (i.e., in an aqueous solution or an organic solvent) oxidation reactions, especially in acidic oxidative environments and in the presence of solvents, reactants, intermediates, or products which solubilize noble metals. The catalyst exhibits significantly improved resistance to noble metal leaching under these conditions. Advantageously, the catalyst additionally exhibits an improved oxidation (i.e., destruction) of the formaldehyde and formic acid by-products during the oxidation of PMIDA to N-(phosphonomethyl)glycine.

The noble metal component of the catalyst serves various functions. For example, depositing a noble metal onto the surface of a catalyst consisting of a carbon support alone tends to reduce the rate of deactivation of the catalyst. To illustrate, when N-(phosphonomethyl)glycine is prepared by the liquid phase oxidative cleav PMIDA with oxygen in the presence of a catalyst consisting of an activated carbon support without a noble metal, the activated carbon is found to deactivate as much as 10% per cycle or more. Without being bound by any particular theory, it is believed that the deactivation of the activated carbon arises because the surface of the carbon support oxidizes under the reaction conditions. See Chou, U.S. Pat. No. 4,624,937. See also, Chou, U.S. Pat. No. 4,696,772, which provides a separate discussion related to deactivation of activated carbon by oxidation of the surface of the carbon. In the presence of the noble metal, however, the rate of deactivation of the activated carbon is diminished. It is believed that the noble metal can react with the oxidant at a faster rate than the activated carbon surface and thus preferentially removes the oxidant from solution before extensive oxidation of the carbon surface can occur. Further, unlike many oxide species which form at activated carbon surfaces and require high temperature treatments to be reduced, oxide species which form at the surface of a noble metal typically are easily reduced by the reducing agents present in or added to the reaction mixture (e.g., the amine fragment cleaved, formaldehyde, formic acid, $H_2$, etc.), thus restoring the noble metal surface to a reduced state. In this manner, the catalyst of this invention advantageously exhibits significantly longer life as long as the noble metal is not lost by leaching, or sintered (i.e., in the form of undesirably thick layers or clumps) by processes such as dissolution and re-deposition or noble metal agglomeration.

Also, depending on the particular oxidation reaction, a noble metal may be more effective than carbon at effecting the oxidation. For example, in the context of the oxidative cleavage of PMIDA to form N-(phosphonomethyl)glycine, although the carbon component of the catalyst primarily effects the oxidation of PMIDA to N-(phosphonomethyl) glycine, it is the noble metal component that primarily effects the oxidation of the undesirable formaldehyde and formic acid by-products into the more preferred by-products, carbon dioxide and water.

It has been discovered in accordance with this invention that oxygen-containing functional groups (e.g., carboxylic acids, ethers, alcohols, aldehydes, lactones, ketones, esters, amine oxides, and amides) at the surface of the carbon support increase noble metal leaching and potentially increase noble metal sintering during liquid phase oxidation reactions and thus reduce the ability of the catalyst to oxidize oxidizable substrates, particularly formaldehyde during the PMIDA oxidation reaction. As used herein, an oxygen-containing functional group is "at the surface of the carbon support" if it is bound to an atom of the carbon support and is able to chemically or physically interact with compositions within the reaction mixture or with the metal atoms deposited on the carbon support.

Many of the oxygen-containing functional groups that reduce noble metal resistance to leaching and sintering and reduce the activity of the catalyst desorb from the carbon support as carbon monoxide when the catalyst is heated at a high temperature (e.g., 900° C.) in an inert atmosphere (e.g., helium or argon). Thus, measuring the amount of CO desorption from a fresh catalyst (i.e., a catalyst that has not previously been used in a liquid phase oxidation reaction) under high temperatures is one method that may be used to analyze the surface of the catalyst to predict noble metal retention and maintenance of catalyst activity. One way to measure CO desorption is by using thermogravimetric analysis with in-line mass spectroscopy ("TGA-MS"). Preferably, no more than about 1.2 mmole of carbon monoxide per gram of catalyst desorb from the catalyst when a dry, fresh sample of the catalyst in a helium atmosphere is subjected to a temperature which is increased from about 20 to about 900° C. at about 10° C. per minute, and then held constant at about 900° C. for about 30 minutes. More preferably, no more than about 0.7 mmole of carbon monoxide per gram of fresh catalyst desorb under those conditions, even more preferably no more than about 0.5 mmole of carbon monoxide per gram of fresh catalyst desorb, and most preferably no more than about 0.3 mmole of carbon monoxide per gram of fresh catalyst desorb. A catalyst is considered "dry" when the catalyst has a moisture content of less than about 1% by weight. Typically, a catalyst may be dried by placing it into a $N_2$ purged vacuum of about 25 inches of Hg and a temperature of about 120° C. for about 16 hours.

Measuring the number of oxygen atoms at the surface of a fresh catalyst support is another method which may be used to analyze the catalyst to predict noble metal retention and maintenance of catalytic activity. Using, for example, x-ray photoelectron spectroscopy, a surface layer of the support which is about 50 Å in thickness is analyzed. Presently available equipment used for x-ray photoelectron spectroscopy typically is accurate to within ±20%. Typically, a ratio of carbon atoms to oxygen atoms at the surface (as measured by presently available equipment for x-ray photoelectron spectroscopy) of at least about 20:1 (carbon atoms:oxygen atoms) is suitable. Preferably, however, the ratio is at least about 30:1, more preferably at least about 40:1, even more preferably at least about 50:1, and most preferably at least about 60:1. In addition, the ratio of oxygen atoms to metal atoms at the surface (again, as measured by presently available equipment for x-ray photoelectron spectroscopy) preferably is less than about 8:1 (oxygen atoms:metal atoms). More preferably, the ratio is less than 7:1, even more preferably less than about 6:1, and most preferably less than about 5:1.

In general, the carbon supports used in the present invention are well known in the art. Activated, a non-graphitized carbon supports are preferred. These supports are characterized by high adsorptive capacity for gases, vapors, and colloidal solids and relatively high specific surface areas. The support suitably may be a carbon, char, or charcoal produced by means known in the art, for example, by destructive distillation of wood, peat, lignite, coal, nut shells, bones, vegetable, or other natural or synthetic carbonaceous matter, but preferably is "activated" to develop adsorptive power. Activation usually is achieved by heating to high temperatures (800–900° C.) with steam or with carbon dioxide which brings about a porous particle structure and increased specific surface area. In some cases, hygroscopic substances, such as zinc chloride and/or phosphoric acid or sodium sulfate, are added before the destructive distillation or activation, to increase adsorptive capacity. Preferably, the carbon content of the carbon support ranges from about 10% for bone charcoal to about 98% for some wood chars and nearly 100% for activated carbons derived from organic polymers. The non-carbonaceous matter in commercially available activated carbon materials normally will vary depending on such factors as precursor origin, processing, and activation method. Many commercially available carbon supports contain small amounts of metals. Carbon supports having the fewest oxygen-containing functional groups at their surfaces are most preferred.

The form of the carbon support is not critical. In one embodiment of this invention, the support is a monolithic support. Suitable monolithic supports may have a wide variety of shapes. Such a support may be, for example, in the form of a screen or honeycomb. Such a support may also, for example, be in the form of a reactor impeller.

In a particularly preferred embodiment, the support are in the form of particulates. Because particulate supports are especially preferred, most of the following discussion focuses on embodiments which use a particulate support. It should be recognized, however, that this invention is not limited to the use of particulate supports.

Suitable particulate supports may have a wide variety of shapes. For example, such supports may be in the form of granules. Even more preferably, the support is in the form of a powder. These particulate supports may be used in a reactor system as free particles, or, alternatively, may be bound to a structure in the reactor system, such as a screen or an impeller.

Typically, a support which is in particulate form comprises a broad size distribution of particles. For powders, preferably at least about 95% of the particles are from about 2 to about 300 μm in their largest dimension, more preferably at least about 98% of the particles are from about 2 to about 200 μm in their largest dimension, and most preferably about 99% of the particles are from about 2 to about 150 μm in their largest dimension with about 95% of the particles being from about 3 to about 100 μm in their largest dimension. Particles being greater than about 200 μm in their largest dimension tend to fracture into super-fine particles (i.e., less than 2 μm in their largest dimension), which are difficult to recover.

The specific surface area of the carbon support, measured by the BET (Brunauer-Emmett-Teller) method using $N_2$, is preferably from about 10 to about 3,000 $m^2/g$ (surface area of carbon support per gram of carbon support), more preferably from about 500 to about 2,100 $m^2/g$, and still more preferably from about 750 to about 2,100 $m^2/g$. In some embodiments, the most preferred specific area is from about 750 to about 1,750 $m^2/g$.

The pore volume of the support may vary widely. Using the measurement method described in Example 1, the pore volume preferably is from about 0.1 to about 2.5 ml/g (pore volume per gram of catalyst), more preferably from about 0.2 to about 2.0 ml/g, and most preferably from about 0.4 to about 1.7 ml/g. Catalysts comprising supports with pore volumes greater than about 2.5 ml/g tend to fracture easily. On the other hand, catalysts comprising supports having pore volumes less than 0.1 ml/g tend to have small surface areas and therefore low activity.

Carbon supports for use in the present invention are commercially available from a number of sources. The following is a listing of some of the activated carbons which may be used with this invention: Darco G-60 Spec and Darco X (ICI-America, Wilmington, Del.); Norit SG Extra, Norit EN4, Norit EXW, Norit A, Norit Ultra-C, Norit ACX, and Norit 4×14 mesh (Amer. Norit Co., Inc., Jacksonville, Fla.); Gl-9615, VG-8408, VG-8590, NB-9377, XZ, NW, and JV (Barnebey-Cheney, Columbus, Ohio); BL Pulv., PWA Pulv., Calgon C 450, and PCB Fines (Pittsburgh Activated Carbon, Div. of Calgon Corporation, Pittsburgh, Pa.); P-100 (No. Amer. Carbon, Inc., Columbus, Ohio); Nuchar CN, Nuchar C-1000 N, Nuchar C-190 A, Nuchar C-115 A, and Nuchar SA-30 (Westvaco Corp., Carbon Department, Covington, Va.); Code 1551 (Baker and Adamson, Division of Allied Amer. Norit Co., Inc., Jacksonville, Fla.); Grade 235, Grade 337, Grade 517, and Grade 256 (Witco Chemical Corp., Activated Carbon Div., New York, N.Y.); and Columbia SXAC (Union Carbide New York, N.Y.).

The catalyst of this invention preferably has one or more noble metal(s) at its surface. Preferably, the noble metal(s) is selected from the group consisting of platinum (Pt), palladium (Pd), ruthenium (Ru), rhodium (Rh), iridium (Ir), silver (Ag), osmium (Os), and gold (Au). In general, platinum and palladium are more preferred, and platinum is most preferred. Because platinum is presently the most preferred noble metal, the following discussion will be directed primarily to embodiments using platinum. It should be understood, however, that the same discussion is generally applicable to the other noble metals and combinations thereof. It also should be understood that the term "noble metal" as used herein means the noble metal in its elemental state as well as the noble metal in any of its various oxidation states.

The concentration of the noble metal deposited at the surface of the carbon support may vary within wide limits. Preferably, it is in the range of from about 0.5 to about 20 wt. % ([mass of noble metal÷total mass of catalyst]×100%), more preferably from about 2.5 to about 10 wt. %, and most preferably from about 3 to about 7.5 wt. %. If concentrations less than 0.5 wt. % are used during the PMIDA oxidation reaction, there tends to be less formaldehyde oxidized, and therefore a greater amount of NMG produced, thereby reducing the N-(phosphonomethyl)glycine yield. On the other hand, at concentrations greater than about 20 wt. %, layers and clumps of noble metal tend to form. Thus, there are fewer surface noble metal atoms per total amount of noble metal used. This tends to reduce the activity of the catalyst and is an uneconomical use of the costly noble metal.

The dispersion of the noble metal at the surface of the carbon support preferably is such that the concentration of surface noble metal atoms is from about 10 to about 400 μmole/g (ymole of surface noble metal atoms per gram of catalyst), more preferably, from about 10 to about 150 μmole/g, and most preferably from about 15 to about 100 μmole/g. This may be determined, for example, by measuring chemisorption of $H_2$ or CO using a Micromeritics ASAP 2010C (Micromeritics, Norcross, Ga.) or an Altamira AMI100 (Zeton Altamira, Pittsburgh, Pa.).

Preferably, the noble metal is at the surface of the carbon support in the form of metal particles. At least about 90% (number density) of the noble metal particles at the surface of the carbon support are preferably from about 0.5 to about 35 nm in their largest dimension, more preferably from about 1 to about 20 nm in their largest dimension, and most preferably from about 1.5 to about 10 nm in their largest dimension. In a particularly preferred embodiment, at least about 80% of the noble metal particles at the surface of the carbon support are from about 1 to about 15 nm in their largest dimension, more preferably from about 1.5 to about 10 nm in their largest dimension, and most preferably from about 1.5 to about 7 nm in their largest dimension. If the noble metal particles are too small, there tends to be an increased amount of leaching when the catalyst is used in an environment that tends to solubilize noble metals, as is the case when oxidizing PMIDA to form N-(phosphonomethyl) glycine. On the other hand, as the particle size increases, there tends to be fewer noble metal surface atoms per total amount of noble metal used. As discussed above, this tends to reduce the activity of the catalyst and is also an uneconomical use of the costly noble metal.

In addition to the noble metal, at least one promoter may be at the surface of the carbon support. Although the promoter typically is deposited onto the surface of the carbon support, other sources of promoter may be used (e.g., the carbon support itself may naturally contain a promoter). A promoter tends to increase catalyst selectivity, activity, and/or stability. A promoter additionally may reduce noble metal leaching.

The promoter may, for example, be an additional noble metal(s) at the surface of the carbon support. For example, ruthenium and palladium have been found to act as promoters on a catalyst comprising platinum deposited at a carbon support surface. The promoter(s) alternatively may be, for example, a metal selected from the group consisting of tin (Sn), cadmium (Cd), magnesium (Mg), manganese (Mn), nickel (Ni), aluminum (Al), cobalt (Co), bismuth (Bi), lead (Pb), titanium (Ti), antimony (Sb), selenium (Se), iron (Fe), rhenium (Re), zinc (Zn), cerium (Ce), and zirconium (Zr). Preferably, the promoter is selected from the group consisting of bismuth, iron, tin, and titanium. In a particularly preferred embodiment, the promoter is tin. In another particularly preferred embodiment, the promoter is iron. In an additional preferred embodiment, the promoter is titanium. In a further particularly preferred embodiment, the catalyst comprises both iron and tin. Use of iron, tin, or both generally (1) reduces noble metal leaching for a catalyst used over several cycles, and (2) tends to increase and/or maintain the activity of the catalyst when the catalyst is used to effect the oxidation of PMIDA. Catalysts comprising iron generally are most preferred because they tend to have the greatest activity and stability with respect to formaldehyde and formic acid oxidation.

In one preferred embodiment, the promoter is more easily oxidized than the noble metal. A promoter is "more easily oxidized" if it has a lower first ionization potential than the noble metal. First ionization potentials for the elements are widely known in the art and may be found, for example, in the *CRC Handbook of Chemistry and Physics* (CRC Press, Inc., Boca Raton, Fla.).

The amount of promoter at the surface of the carbon support (whether associated with the carbon surface itself, metal, or a combination thereof) may vary within wide limits depending on, for example, the noble metal and promoter used. Typically, the weight percentage of the promoter is at least about 0.05% ([mass of promoter÷total mass of the catalyst]×100%). The weight percent of the promoter preferably is from about 0.05 to about 10%, more preferably from about 0.1 to about 10%, still more preferably from about 0.1 to about 2%, and most preferably from about 0.2 to about 1.5%. When the promoter is tin, the weight percent most preferably is from about 0.5 to about 1.5%. Promoter weight percentages less than 0.05% generally do not promote the activity of the catalyst over an extended period of time. On the other hand, weight percents greater than about 10% tend to decrease the activity of the catalyst.

The molar ratio of noble metal to promoter may also vary widely, depending on, for example, the noble metal and promoter used. Preferably, the ratio is from about 1000:1 to about 0.01:1; more preferably from about 150:1 to about 0.05:1; still more preferably from about 50:1 to about 0.05:1; and most preferably from about 10:1 to about 0.05:1. For example, a catalyst comprising platinum and iron preferably has a molar ratio of platinum to iron of about 3:1.

In a particularly preferred embodiment of this invention, the noble metal (e.g., Pt) is alloyed with at least one promoter (e.g., Sn, Fe, or both) to form alloyed metal particles. A catalyst comprising a noble metal alloyed with at least one promoter tends to have all the advantages discussed above with respect to catalysts comprising a promoter. It has been found in accordance with this invention, however, that catalysts comprising a noble metal alloyed with at least one promoter tend to exhibit greater resistance to promoter leaching and further stability from cycle to cycle with respect to formaldehyde and formic acid oxidation. See, e.g., Example 17.

The term "alloy" encompasses any metal particle comprising a noble metal and at least one promoter, irrespective of the precise manner in which the noble metal and promoter atoms are disposed within the particle (although it is generally preferable to have a portion of the noble metal atoms at the surface of the alloyed metal particle). The alloy may be, for example, any of the following:

1. An intermetallic compound. An intermetallic compound is compound comprising a noble metal and a promoter (e.g., $Pt_3Sn$)
2. A substitutional alloy. A substitutional alloy has a single, continuous phase, irrespective of the concentrations of the noble metal and promoter atoms. Typically, a substitutional alloy contains noble metal and promoter atoms which are similar in size (e.g., platinum and silver; or platinum and palladium). Substitutional alloys are also referred to as "monophasic alloys."
3. A multiphasic alloy. A multiphasic alloy is an alloy that contains at least two discrete phases. Such an alloy may contain, for example $Pt_3Sn$ in one phase, and tin dissolved in platinum in a separate phase.
4. A segregated alloy. A segregated alloy is a metal particle wherein the particle stoichiometry varies with distance from the surface of the metal particle.
5. An interstitial alloy. An interstitial alloy is a metal particle wherein the noble metal and promoter atoms are combined with non-metal atoms, such as boron, carbon, silicon, nitrogen, phosphorus, etc.

Preferably, at least about 80% (number density) of the alloyed metal particles are from about 0.5 to about 35 nm in their largest dimension, more preferably from about 1 to about 20 nm in their largest dimension, still more preferably from about 1 to about 15 nm in their largest dimension, and most preferably from about 1.5 to about 7 nm in their largest dimension.

The alloyed metal particles need not have a uniform composition; the compositions may vary from particle to particle, or even within the particles themselves. In addition, the catalyst may further comprise particles consisting of the noble metal alone or the promoter alone. Nevertheless, it is preferred that the composition of metal particles be substantially uniform from particle to particle and within each particle, and that the number of noble metal atoms in intimate contact with promoter atoms be maximized. It is also preferred, although not essential, that the majority of noble metal atoms be alloyed with a promoter, and more preferred that substantially all of the noble metal atoms be alloyed with a promoter. It is further preferred, although not essential, that the alloyed metal particles be uniformly distributed at the surface of the carbon support.

Regardless of whether the promoter is alloyed to the noble metal, it is presently believed that the promoter tends to become oxidized if the catalyst is exposed to an oxidant over a period of time. For example, an elemental tin promoter tends to oxidize to form $Sn(II)O$, and $Sn(II)O$ tends to oxidize to form $Sn(IV)O_2$. This oxidation may occur, for example, if the catalyst is exposed to air for more than about 1 hour. Although such promoter oxidation has not been observed to have a significant detrimental effect on noble metal leaching, noble metal sintering, catalyst activity, or catalyst stability, it does make analyzing the concentration of detrimental oxygen-containing functional groups at the surface of the carbon support more difficult. For example, as discussed above, the concentration of detrimental oxygen-containing functional groups (i.e., oxygen-containing functional groups that reduce noble metal resistance to leaching and sintering, and reduce the activity of the catalyst) may be determined by measuring (using, for example, TGA-MS) the amount of CO that desorbs from the catalyst under high temperatures in an inert atmosphere. However, it is presently believed that when an oxidized promoter is present at the surface, the oxygen atoms from the oxidized promoter tend to react with carbon atoms of the support at high temperatures in an inert atmosphere to produce CO, thereby creating the illusion of more detrimental oxygen-containing functional groups at the surface of the support than actually exist. Such oxygen atoms of an oxidized promoter also can interfere with obtaining a reliable prediction of noble metal leaching, noble metal sintering, and catalyst activity from the simple measurement (via, for example, x-ray photoelectron spectroscopy) of oxygen atoms at the catalyst surface.

Thus, when the catalyst comprises at least one promoter which has been exposed to an oxidant and thereby has been oxidized (e.g., when the catalyst has been exposed to air for more than about 1 hour), it is preferred that the promoter first be substantially reduced (thereby removing the oxygen atoms of the oxidized promoter from the surface of the catalyst) before attempting to measure the amount of detrimental oxygen-containing functional groups at the surface of the carbon support. This reduction preferably is achieved by heating the catalyst to a temperature of about 500° C. for about 1 hour in an atmosphere consisting essentially of $H_2$. The measurement of detrimental oxygen-containing functional groups at the surface preferably is performed (a) after this reduction, and (b) before the surface is exposed to an oxidant following the reduction. Most preferably, the measurement is taken immediately after the reduction.

The preferred concentration of metal particles at the surface of the carbon support depends, for example, on the size of the metal particles, the specific surface area of the carbon support, and the concentration of noble metal on the catalyst. It is presently believed that, in general, the preferred concentration of metal particles is roughly from about 3 to about 1,500 particles/$\mu m^2$ (i.e., number of metal particles per $\mu m^2$ of surface of carbon support), particularly where: (a) at least about 80% (number density) of the metal particles are from about 1.5 to about 7 nm in their largest dimension, (b) the carbon support has a specific surface area of from about 750 to about 2100 $m^2$/g (i.e., $m^2$ of surface of carbon support per gram of carbon support), and (c) the concentration of noble metal at the carbon support surface is from about 1 to about 10 wt. % ([mass of noble metal÷total mass of catalyst]×100%). In more preferred embodiments, narrower ranges of metal particle concentrations and noble metal concentrations are desired. In one such embodiment, the concentration of metal particles is from about 15 to about 800 particles/$\mu m^2$, and the concentration of noble metal at the carbon support surface is from about 2 to about 10 wt. %. In an even more preferred embodiment, the concentration of metal particles is from about 15 to about 600 particles/$\mu m^2$, and the concentration of noble metal at the carbon support surface is from about 2 to about 7.5 wt. %. In the most preferred embodiment, the concentration of the metal particles is from about 15 to about 400 particles/$\mu m^2$, and the concentration of noble metal at the carbon support surface is about 5 wt. %. The concentration of metal particles at the surface of the carbon support may be measured using methods known in the art.

B. Process for the Preparation of the Oxidation Catalyst

1. Deoxygenation of the Carbon Support

The surface of the carbon support preferably is deoxygenated before the noble metal is deposited onto it. Preferably, the surface is deoxygenated using a high-temperature deoxygenation treatment. Such a treatment may be a single-step or a multi-step scheme which, in either case, results in an overall chemical reduction of oxygen-containing functional groups at the surface of the carbon support.

In a two-step high-temperature deoxygenation treatment, the carbon support preferably is first treated with a gaseous or liquid phase oxidizing agent to convert oxygen-containing functionalities in relatively lower oxidation states (e.g., ketones, aldehydes, and alcohols) into functionalities in relatively higher oxidation states (e.g., carboxylic acids), which are easier to cleave from the surface of the catalyst at high temperatures. Representative liquid phase oxidizing agents include nitric acid, $H_2O_2$, chromic acid, and hypochlorite, with concentrated nitric acid comprising from about 10 to about 80 grams of $HNC_3$ per 100 grams of aqueous solution being preferred. Representative gaseous oxidants include molecular oxygen, ozone, nitrogen dioxide, and nitric acid vapors. Nitric acid vapors are the preferred oxidizing agent. With a liquid oxidant, temperatures of from about 60 to about 90° C. are appropriate, but with gaseous oxidants, it is often advantageous to use temperatures from about 50 to about 500° C. or even greater. The time during which the carbon is treated with the oxidant can vary widely from about 5 minutes to about 10 hours. Preferably, the reaction time is from about 30 minutes to about 6 hours. Experimental results indicate that carbon load, temperature, oxidant concentration, etc. in the first treatment step are not narrowly critical to achieving the desired oxidation of the carbon material and thus may be governed by convenience over a wide range. The highest possible carbon load is preferred for economic reasons.

In the second step, the oxidized carbon support is pyrolyzed (i.e., heated) at a temperature preferably in the range of from about 500 to about 1500° C., and more preferably from about 600 to about 1,200° C., in a nitrogen, argon, helium, or other non-oxidizing environment (i.e., an environment consisting essentially of no oxygen) to drive off the oxygen-containing functional groups from the carbon surface. At temperatures greater than 500° C., an environment may be used which comprises a small amount of ammonia (or any other chemical entity which will generate $NH_3$ during pyrolysis), steam, or carbon dioxide which aid in the pyrolysis. As the temperature of the carbon support is cooled to temperatures less than 500° C., however, the presence of oxygen-containing gases such as steam or carbon dioxide may lead to the re-formation of surface oxides and thus, is preferably avoided. Accordingly, the pyrolysis is preferably conducted in a non-oxidizing atmosphere (e.g., nitrogen, argon, or helium). In one embodiment, the non-oxidizing atmosphere comprises ammonia, which tends to produce a more active catalyst in a shorter time as compared to pyrolysis in the other atmospheres. The pyrolysis may be achieved, for example, using a rotary kiln, a fluidized bed reactor, or a conventional furnace.

The carbon support generally is pyrolyzed for a period of from about 5 minutes to about 60 hours, preferably from about 10 minutes to about 6 hours. Shorter times are preferred because prolonged exposure of the carbon at elevated temperatures tends to reduce the activity of the catalyst. Without being bound to any particular theory, it is presently believed that prolonged heating at pyrolytic temperatures favors the formation of graphite, which is a less preferred form of a carbon support because it normally has less surface area. As discussed above, a more active catalyst typically may be produced in a shorter time by using an atmosphere which comprises ammonia.

In a preferred embodiment of this invention, high-temperature deoxygenation is carried out in one step. This one-step treatment may consist of merely performing the pyrolysis step of the two-step high-temperature deoxygenation treatment discussed above. More preferably, however, the single-step treatment consists of pyrolyzing the carbon support as described above while simultaneously passing a gas stream comprising $N_2$, $NH_3$ (or any other chemical entity which will generate $NH_3$ during pyrolysis), and steam over the carbon. Although it is not a critical feature of this invention, the flow rate of the gas stream preferably is fast enough to achieve adequate contact between the fresh gas reactants and the carbon surface, yet slow enough to prevent excess carbon weight loss and material waste. A non-reactive gas may be used as a diluent to prevent severe weight loss of the carbon.

2. Deposition of the Noble Metal(s)

Methods used to deposit the noble metal onto the surface of the carbon support are generally known in the art, and include liquid phase methods such as reaction deposition techniques (e.g., deposition via reduction of noble metal compounds, and deposition via hydrolysis of noble metal compounds), ion exchange techniques, excess solution impregnation, and incipient wetness impregnation; vapor phase methods such as physical deposition and chemical deposition; precipitation; electrochemical deposition; and electroless deposition. See generally, Cameron, D. S., Cooper, S. J., Dodgson, I. L., Harrison, B., and Jenkins, J. W. "Carbons as Supports for Precious Metal Catalysts," *Catalysis Today*, 7, 113–137 (1990). Catalysts comprising noble metals at the surface of a carbon support also are commercially available, e.g., Aldrich Catalog No. 20,593-1, 5% platinum on activated carbon (Aldrich Chemical Co., Inc., Milwaukee, Wis.); Aldrich Catalog No. 20,568-0, 5% palladium on activated carbon.

Preferably, the noble metal is deposited via a reactive deposition technique comprising contacting the carbon support with a solution comprising a salt of the noble metal, and then hydrolyzing the salt. An example of a suitable platinum salt which is relatively inexpensive is hexachloroplatinic acid ($H_2PtCl_6$). The use of this salt to deposit platinum onto a carbon support via hydrolytic deposition is illustrated in Example 3.

In one embodiment of this invention, the noble metal is deposited onto the surface of the carbon support using a solution comprising a salt of a noble metal in one of its more reduced oxidation states. For example, instead of using a salt of Pt (IV) (e.g., $H_2PtCl_6$), a salt of Pt (II) is used. In another embodiment, platinum in its elemental state (e.g., colloidal platinum) is used. Using these more reduced metal precursors leads to less oxidation of the carbon support and, therefore, less oxygen-containing functional groups being formed at the surface of the support while the noble metal is being deposited onto the surface. One example of a Pt(II) salt is $K_2PtCl_4$. Another potentially useful Pt(II) salt is diamminedinitrito platinum(II). Example 11 shows that using this salt to deposit the noble metal produces a catalyst which is more resistant to leaching than a catalyst prepared using $H_2PtCl_6$ as the metal precursor. Without being bound by any particular theory, it is believed that this is due to the fact that diamminedinitrito platinum(II) generates ammonia in-situ during reduction which further promotes removal of the oxygen-containing functional groups at the surface of the carbon support. This benefit, however, should be weighed against a possible explosion danger associated with the use of diamminedinitrito platinum(II).

3. Deposition of the Promoter(s)

A promoter(s) may be deposited onto the surface of the carbon support before, simultaneously with, or after deposition of the noble metal onto the surface. Methods used to deposit a promoter onto the surface of the carbon support are generally known in the art, and include the same methods used to deposit a noble metal discussed above. In one embodiment, a salt solution comprising the promoter is used to deposit the promoter. A suitable salt that may be used to deposit bismuth is $Bi(NO_3)_3 \cdot 5H_2O$, a suitable salt that may be used to deposit iron is $FeCl_3 \cdot 6H_2O$, and a suitable salt that may be used to deposit tin is $SnCl_2 \cdot 2H_2O$. It should be recognized that more than one promoter may be deposited onto the surface of the carbon support. Examples 13, 14, 15, and 17 demonstrate depositing a promoter onto a carbon surface with a salt solution comprising a promoter. Example 18 demonstrates depositing more than one promoter (i.e., iron and Sn) onto a carbon surface using salt solutions comprising the promoters.

As noted above, a catalyst comprising a noble metal alloyed with at least one promoter is particularly preferred. There are a variety of possible preparative techniques known in the art which may be used to form a multi-metallic alloy at support surfaces. See, e.g., V. Ponec & G. C. Bond, *Catalysis by Metals and Alloys*, "Studies in Surface Science and Catalysis," Vol. 95 (B. Delmon. & J. T. Yates, advisory eds., Elsevier Science B.V., Amsterdam, Netherlands).

In one of the more preferred embodiments, reactive deposition is used to form metal particles containing a noble metal alloyed with a promoter. Reactive deposition may comprise, for example, reductive deposition wherein a surface of a carbon support is contacted with a solution comprising: (a) a reducing agent; and (b) (i) a compound comprising the noble metal and a compound comprising the promoter, or (ii) a compound comprising both the noble metal and the promoter. A wide range of reducing agents may be used, such as sodium borohydride, formaldehyde, formic acid, sodium formate, hydrazine hydrochloride, hydroxylamine, and hypophosphorous acid. Compounds comprising a noble metal and/or a promoter include, for example:

1. Halide compounds. These include, for example, $H_2PtCl_6$, $K_2PtCl_4$, $Pt_2Br_6^{2-}$, $K_2PdCl_4$, $AuCl_4^{1-}$, $RuCl_3$, $RhCl_3 \cdot 3H_2O$, $K_2RuCl_6$, $FeCl_3 \cdot 6H_2O$, $(SnCl_3)^{1-}$, $SnCl_4$, $ReCl_6$, $FeCl_2$, and $TiCl_4$.

2. Oxide and oxy chloride compounds. These include, for example, $RuO_4^{2-}$ and $M_2SnO_4$.

3. Nitrate compounds. These include, for example, $Fe(NO_3)_3$.

4. Amine complexes. These include, for example, [Pt($NH_3$)$_4$]Cl$_2$, [Pd($NH_3$)$_4$]Cl$_2$, Pt($NH_3$)$_2$Cl$_2$, Pt($NH_3$)$_4$]PtCl$_4$, Pd($NH_2CH_2CH_2NH_2$) C$_{12}$, Pt($NH_2CH_2CH_2NH_2$)$_2$Cl$_2$, and [Ru($NH_3$)$_5$Cl]Cl$_2$.

5. Phosphine complexes. These include, for example, Pt(P(CH$_3$)$_3$)$_2$Cl$_2$; IrClCO(P(C$_6$H$_5$)$_3$)$_2$; PtClH(PR$_3$)$_2$, wherein each R is independently a hydrocarbyl, such as methyl, ethyl, propyl, phenyl, etc 6. Organometallic complexes. These include, for example, $Pt_2(C_3H_6)_2Cl_4$; $Pd_2(C_2H_4)_2Cl_4$; $Pt(CH_3COO)_2$, $Pd(CH_3COO)_2$; $K[Sn(HCOO)_3]$; $Fe(CO)_5$; $Fe_3(CO)_{12}$; $Fe_4(CO)_{16}$; $Sn_3(CH_3)_4$; and $Ti(OR)_4$, wherein each R is independently a hydrocarbyl, such as methyl, ethyl, propyl, phenyl, etc.

7. Noble metal/promoter complexes. These include, for example, $Pt_3(SnCl_3)_2(C_8H_{12})_3$ and $[Pt(SnCl_3)_5]^{3-}$.

In a particularly preferred embodiment, hydrolysis reactions are used to deposit a noble metal alloyed with a promoter. In this instance, ligands containing the noble metal and promoter are formed, and then hydrolyzed to form well-mixed, metal oxide and metal hydroxide clusters at the surface of the carbon support. The ligands may be formed, for example, by contacting the surface of the support with a solution comprising (a) a compound comprising the noble metal and a compound comprising the promoter, or (b) a compound comprising both the noble metal and the promoter. Suitable compounds comprising a noble metal and/or a promoter are listed above with respect to reductive deposition. Hydrolysis of the ligands may be achieved, for example, by heating (e.g., at a temperature of at least about 60° C.) the mixture. Example 17 further demonstrates the use of hydrolysis reactions to deposit a noble metal (i.e., platinum) alloyed with a promoter (i.e., iron).

In addition to the above-described reactive deposition techniques, there are many other techniques which may be used to form the alloy. These include, for example:

1. Forming the alloy by introducing metal compounds (which may be simple or complex, and may be covalent or ionic) to the surface of the support via impregnation, adsorption from a solution, and/or ion exchange.
2. Forming the alloy by vacuum co-deposition of metal vapors containing the noble metal and promoter onto the surface.
3. Forming the alloy by depositing one or metals onto a pre-deposited metal belonging to Group 8, 9, or 10 of the Periodic Table of the Elements (i.e., Fe, Co, Ni, Ru, Rh, Pd, Os, Ir, and Pt) via, for example, electrolytic or electroless plating.
4. Forming the alloy by: (a) depositing metal complexes containing metals in the zero valence state (e.g., carbonyl, pi-allyl, or cyclopentadienyl complexes of the noble metal and of the promoter) at the surface of the carbon support; and (b) removing the ligands by, for example, heating or reduction to form the alloy particles at the surface.
5. Forming the alloy by contacting a solution containing a metal compound (e.g., a metal chloride or a metal alkyl compound) with a pre-deposited metal hydride containing a metal belonging to Group 8, 9, or 10 of the Periodic Table of the Elements.
6. Forming the alloy by co-depositing, either simultaneously or sequentially, metal complexes (either preformed or formed in situ) containing the noble metal(s) and promoter(s) at the surface of the carbon support.
7. Forming the alloy by pre-forming alloy particles as colloids or aerosols, and then depositing the preformed alloy particles at the surface of the carbon support. To illustrate, colloidal particles containing platinum and iron may be easily formed by boiling a dilute solution of $H_2PtCl_6$ and $SnCl_2.2H_2O$ with a sodium citrate solution. Protecting agents (e.g., carbohydrates, polymers, lipophilic quaternary nitrogen salts) may be used to effectively control metal alloy particle growth. This technique, therefore, is often useful to form a narrow distribution of alloy particle sizes.

It should be recognized that the above-discussed techniques for forming an alloy are simply illustrative, and not exhaustive. Using the teachings of this specification and the general knowledge of the art, one of ordinary skill in the art may routinely determine which of the numerous alloy preparation techniques known in the art are suitable to a particular use.

Regardless of the technique used to form the alloy, after the metals have been deposited at the surface of the carbon support, it is often preferable to dry the support using, for example, a sub-atmospheric, non-oxidizing environment (preferably, $N_2$, a noble gas, or both). Use of a drying step is particularly preferred where the surface of the support is to be subsequently reduced by heating the surface (and even more preferred where the heating is to be conducted in a non-oxidizing environment). Preferably, the support is dried to reduce the moisture content of the support to less than about 5% by weight.

It should be recognized that reducing the surface of the carbon support after deposition of the noble metal(s) and promoter(s) typically increases the extent of noble metal alloyed with a promoter. Such reduction also often tends to increase the number of particles falling within the preferred size range.

4. Reduction of the Carbon Support Surface

After the carbon support has been impregnated with the noble metal(s) (and promoter(s), if any), the surface of the catalyst preferably is reduced. The surface of the catalyst suitably may be reduced, for example, by heating the surface at a temperature of at least about 400° C. It is especially preferable to conduct this heating in a non-oxidizing environment (e.g., nitrogen, argon, or helium). It is also more preferred for the temperature to be greater than about 500° C. Still more preferably, the temperature is from about 550 to about 1,200° C., and most preferably from about 550 to about 900° C. Temperatures less than 400° C. tend to be unsatisfactory for removing the oxygen-containing functional groups from the surface of the carbon support. On the other hand, temperatures greater than 1,200° C. tend to reduce the activity of the catalyst. Temperatures of from about 400 to about 500° C. preferably are used only if the surface of the carbon support has a carbon atom to oxygen atom ratio of at least about 20:1 before the noble metal is deposited onto the surface.

In a particularly preferred embodiment, the surface of the catalyst is reduced by a process comprising exposing the surface to a reducing environment. For example, before the heating, the catalyst sample may be pre-treated with a liquid-phase reducing agent, such as formaldehyde or formic acid. Even more preferably, the heating is conducted in the presence of a gas-phase reducing agent (the method of heating the catalyst in the presence of a gas-phase reducing agent will sometimes be referred to as "high-temperature gas-phase reduction"). Various gas-phase reducing agents may be used during the heating, including but not limited to $H_2$, ammonia, and carbon monoxide. Hydrogen gas is most preferred because the small molecular size of hydrogen allows better penetration into the deepest pores of the carbon support. Preferably, the remainder of the gas consists essentially of a non-oxidizing gas, such as nitrogen, argon, or helium. The gas may comprise any finite concentration of $H_2$, although $H_2$ concentrations of less than 1.0% are disadvantageous because of the time they tend to require to reduce the surface of the support. Preferably, the gas comprises from about 5 to about 50 volume % $H_2$, and most preferably from about 5 to about 25 volume % $H_2$.

The preferred amount of time that the catalyst surface is heated depends on the mass transfer of the reducing agent to the catalyst surface. When the reducing agent is a non-oxidizing gas comprising from about 10 to about 20 volume % $H_2$, the surface preferably is heated for from about 15 minutes to about 24 hours at from about 550 to about 900° C. with a space velocity of from about 1 to about 5,000 $hour^{-1}$. More preferably, the space velocity is from about 10 to about 2,500 $hour^{-1}$, and even more preferably from about 50 to about 750 $hour^{-1}$. In the most preferred embodiment, the heat-treatment is conducted at the above preferred temperatures and space velocities for from about 1 to about 10 hours. Heating the surface at space velocities of less than 1 $hour^{-1}$ is disadvantageous because the oxygen-containing functional groups at the surface of the carbon support may not be sufficiently destroyed. On the other hand, heating the surface at space velocities greater than 5,000 $hour^{-1}$ is uneconomical.

In accordance with this invention it has been found that pre-existing oxygen-containing functional groups at the surface of the carbon support are not necessary, or even desired, to obtain adequate noble metal dispersion and retention. Without being bound by any particular theory, it is believed that this heating step enhances the platinum-carbon interaction on the catalyst by removing oxygen-containing functional groups at the surface of the carbon support, including those formed by depositing the noble metal onto the surface. It is believed that these oxygen-containing functional groups are unstable anchor sites for the noble metal because they tend to interfere with the potentially stronger n interactions between the noble metal and the carbon support. Heating alone will decompose and thereby remove many of the oxygen-containing functional groups at the surface of the carbon support. However, by heating the surface in the presence of a reducing agent (e.g., $H_2$), more oxygen-containing functional groups are able to be eliminated.

If the carbon atom to oxygen atom ratio at the surface of the carbon support is less than about 20:1 before the noble metal is deposited onto the surface of the support, the surface preferably is reduced using the above-described high-temperature gas-phase reduction treatment at a temperature greater than 500° C., although the surface may optionally be treated with other reduction environments in addition to high-temperature gas-phase reduction. On the other hand, if the surface of the carbon support has a carbon atom to oxygen atom ratio which is at least about 20:1 before the noble metal is deposited onto the surface, various alternative reduction environments may be used instead of high-temperature gas-phase reduction.

The surface of the catalyst may be reduced, at least in part, by treating it with an amine, such as urea, a solution comprising ammonium ions (e.g., ammonium formate or ammonium oxalate), or ammonia gas, with ammonia gas or a solution comprising ammonium ions being most preferred. This amine treatment preferably is used in addition to other reduction treatments, and most preferably is used before high-temperature gas-phase reduction. In one such embodiment, the noble metal is deposited onto the surface by treating it with a noble metal precursor solution comprising ammonium ions. Alternatively, after the noble metal is deposited onto the surface of the support, the support may be washed with a solution comprising ammonium ions or placed into contact with a gas comprising ammonia. Most preferably, the catalyst surface is washed with diluted aqueous ammonia after depositing the noble metal. In this instance, the catalyst is added to pure water and stirred for a few hours to wet the surface of the catalyst. Next, while continuing to stir the catalyst slurry, a solution comprising ammonium ions is added to the catalyst slurry in an amount sufficient to produce a pH of greater than 7, more preferably from about 8 to about 12, and most preferably from about 9.5 to about 11.0. Because the temperature and pressure are not critical, this step preferably is performed at room temperature and atmospheric pressure. Example 10 further demonstrates this reduction treatment.

Sodium borohydride ($NaBH_4$) also may be used to reduce the surface of the catalyst. As with the amine treatment, this treatment preferably is used in addition to other reduction treatments, and most preferably is used before high-temperature gas-phase reduction. Preferably, after depositing the noble metal onto the surface of the support, the support is washed with a solution of $NaBH_4$ in the presence of NaOH at a pH of from about 8 to about 14 for about 15 to about 180 minutes. The amount of $NaBH_4$ used preferably is sufficient to reduce all the noble metal. Because the temperature and pressure are not critical, this step preferably is performed at room temperature and atmospheric pressure. Example 12 further demonstrates this reduction treatment.

It should be recognized that any of the above treatments which may be used to reduce the surface of the catalyst also may be used to deoxygenate the surface of the carbon support before the noble metal is deposited onto the surface.

C. Use of the Oxidation Catalyst

The above-described catalyst may be used for liquid phase oxidation reactions. Examples of such reactions include the oxidation of alcohols and polyols to form aldehydes, ketones, and acids (e.g., the oxidation of 2-propanol to form acetone, and the oxidation of glycerol to form glyceraldehyde, dihydroxyacetone, or glyceric acid); the oxidation of aldehydes to form acids (e.g., the oxidation of formaldehyde to form formic acid, and the oxidation of furfural to form 2-furan carboxylic acid); the oxidation of tertiary amines to form secondary amines (e.g., the oxidation of nitrilotriacetic acid ("NTA") to form iminodiacetic acid ("IDA")); the oxidation of secondary amines to form primary amines (e.g., the oxidation of IDA to form glycine); and the oxidation of various acids (e.g., formic acid or acetic acid) to form carbon dioxide and water.

The above-described catalyst is especially useful in liquid phase oxidation reactions at pH levels less than 7, and in particular, at pH levels less than 3. It also is especially useful in the presence of solvents, reactants, intermediates, or products which solubilize noble metals. One such reaction is the oxidation of PMIDA or a salt thereof to form N-(phosphonomethyl)glycine or a salt thereof in an environment having pH levels in the range of from about 1 to about 2. The description below will disclose with particularity the use of the above-described catalyst to effect the oxidative cleavage of PMIDA or a salt thereof to form N-(phosphonomethyl)glycine or a salt thereof. It should be recognized, however, that the principles disclosed below are generally applicable to other liquid phase oxidative reactions, especially those at pH levels less than 7 and those involving solvents, reactants, intermediates, or products which solubilize noble metals.

To begin the PMIDA oxidation reaction, it is preferable to charge the reactor with the PMIDA reagent (i.e., PMIDA or a salt thereof), catalyst, and a solvent in the presence of oxygen. The solvent is most preferably water, although other solvents (eag., glacial acetic acid) are suitable as well.

The reaction may be carried out in a wide variety of batch, semi-batch, and continuous reactor systems. The configuration of the reactor is not critical. Suitable conventional reactor configurations include, for example, stirred tank reactors, fixed bed reactors, trickle bed reactors, fluidized bed reactors, bubble flow reactors, plug flow reactors, and parallel flow reactors.

When conducted in a continuous reactor system, the residence time in the reaction zone can vary widely depending on the specific catalyst and conditions employed. Typically, the residence time can vary over the range of from about 3 to about 120 minutes. Preferably, the residence time is from about 5 to about 90 minutes, and more preferably from about 5 to about 60 minutes. When conducted in a batch reactor, the reaction time typically varies over the range of from about 15 to about 120 minutes. Preferably, the reaction time is from about 20 to about 90 minutes, and more preferably from about 30 to about 60 minutes.

In a broad sense, the oxidation reaction may be practiced in accordance with the present invention at a wide range of temperatures, and at pressures ranging from sub-atmospheric to super-atmospheric. Use of mild conditions (e.g., room temperature and atmospheric pressure) have obvious commercial advantages in that less expensive equipment may be used. However, operating at higher temperatures and super-atmospheric pressures, while increasing plant costs, tends to improve phase transfer between the liquid and gas phase and increase the PMIDA oxidation reaction rate.

Preferably, the PMIDA reaction is conducted at a temperature of from about 20 to about 180° C., more preferably from about 50 to about 140° C., and most preferably from about 80 to about 110° C. At temperatures greater than about 180° C., the raw materials tend to begin to slowly decompose.

The pressure used during the PMIDA oxidation generally depends on the temperature used. Preferably, the pressure is sufficient to prevent the reaction mixture from boiling. If an oxygen-containing gas is used as the oxygen source, the pressure also preferably is adequate to cause the oxygen to dissolve into the reaction mixture at a rate sufficient such that the PMIDA oxidation is not limited due to an inadequate oxygen supply. The pressure preferably is at least equal to atmospheric pressure. More preferably, the pressure is from about 30 to about 500 psig, and most preferably from about 30 to about 130 psig.

The catalyst concentration preferably is from about 0.1 to about 10 wt. % ([mass of catalyst÷total reaction mass]× 100%). More preferably, the catalyst concentration preferably is from about 0.2 to about 5 wt. %, and most preferably from about 0.3 to about 1.5 wt. %. Concentrations greater than about 10 wt. % are difficult to filter. On the other hand, concentrations less than about 0.1 wt. % tend to produce unacceptably low reaction rates.

The concentration of PMIDA reagent in the feed stream is not critical. Use of a saturated solution of PMIDA reagent in water is preferred, although for ease of operation, the process is also operable at lesser or greater PMIDA reagent concentrations in the feed stream. If the catalyst is present in the reaction mixture in a finely divided form, it is preferred to use a concentration of reactants such that all reactants and the N-(phosphonomethyl)glycine product remain in solution so that the catalyst can be recovered for re-use, for example, by filtration. On the other hand, greater concentrations tend to increase reactor through-put. Alternatively, if the catalyst is present as a stationary phase thrpugh which the reaction medium and oxygen source are passed, it may be possible to use greater concentrations of reactants such that a portion of the N-(phosphonomethyl)glycine product precipitates.

It should be recognized that, relative to many commonly-practiced commercial processes, this invention allows for greater temperatures and PMIDA reagent concentrations to be used to prepare N-(phosphonomethyl)glycine while minimizing by-product formation. In the commonly practiced commercial processes using a carbon-only catalyst, it is economically beneficial to minimize the formation of the NMG by-product formed by the reaction of N-(phosphonomethyl)glycine with the formaldehyde by-product. With these processes and catalysts, temperatures of from about 60 to 90° C. and PMIDA reagent concentrations below about 9.0 wt. % ([mass of PMIDA reagent÷total reaction mass]×100%) typically are used to achieve cost effective yields and to minimize the generation of waste. At these temperatures, the maximum N-(phosphonomethyl) glycine solubility typically is less than 6.5%. However, with the oxidation catalyst and reaction process of this invention, the loss of noble metal from the catalyst and catalyst deactivation have been minimized and the formaldehyde is more effectively oxidized, thereby allowing for reaction temperatures as high as 180° C. or greater with PMIDA reagent solutions and slurries of the PMIDA reagent. The use of higher temperatures and reactor concentrations permits reactor throughput to be increased, reduces the amount of water that must be removed before isolation of the solid N-(phosphonomethyl)glycine, and reduces the cost of manufacturing N-(phosphonomethyl)glycine. This invention thus provides economic benefits over many commonly-practiced commercial processes.

Normally, a PMIDA reagent concentration of up to about 50 wt. % ([mass of PMIDA reagent÷total reaction mass]× 100%) may be used (especially at a reaction temperature of from about 20 to about 180° C.). Preferably, a PMIDA reagent concentration of up to about 25 wt. % is used (particularly at a reaction temperature of from about 60 to about 150° C.). More preferably, a.PMIDA reagent concentration of from about 12 to about 18 wt. % is used (particularly at a reaction temperature of from about 100 to about 130° C.). PMIDA reagent concentrations below 12 wt. % may be used, but their use is less economical because less N-(phosphonomethyl)glycine product is produced in each reactor cycle and more water must be removed and energy used per unit of N-(phosphonomethyl)glycine product produced. Lower temperatures (i.e., temperatures less than 100° C.) often tend to be less advantageous because the solubility of the PMIDA reagent and N-(phosphonomethyl)glycine product are both reduced at such temperatures.

The oxygen source for the PMIDA oxidation reaction may be any oxygen-containing gas or a liquid comprising dissolved oxygen. Preferably, the oxygen source is an oxygen-containing gas. As used herein, an "oxygen-containing gas" is any gaseous mixture comprising molecular oxygen which optionally may comprise one or more diluents which are non-reactive with the oxygen or with the reactant or product under the reaction conditions. Examples of such gases are air, pure molecular oxygen, or molecular oxygen diluted with helium, argon, nitrogen, or other non-oxidizing gases. For economic reasons, the oxygen source most preferably is air or pure molecular oxygen.

The oxygen may be introduced by any conventional means into the reaction medium in a manner which maintains the dissolved oxygen concentration in the reaction mixture at the desired level. If an oxygen-containing gas is used, it preferably is introduced into the reaction medium in a manner which maximizes the contact of the gas with the reaction solution. Such contact may be obtained, for example, by dispersing the gas through a diffuser such as a porous frit or by stirring, shaking, or other methods known to those skilled in the art.

The oxygen feed rate preferably is such that the PMIDA oxidation reaction rate is not limited by oxygen supply. If the dissolved oxygen concentration is too high, however, the catalyst surface.tends to become detrimentally oxidized, which, in turn, tends to lead to more leaching and decreased formaldehyde activity (which, in turn, leads to more NMG being produced).

Generally, it is preferred to use an oxygen feed rate such that at least about 40% of the oxygen is utilized. More preferably, the oxygen feed rate is such that at least about 60% of the oxygen is utilized. Even more preferably, the oxygen feed rate is such that at least about 80% of the oxygen is utilized. Most preferably, the rate is such that at least about 90% of the oxygen is utilized. As used herein, the percentage of oxygen utilized equals: (the total oxygen consumption rate÷oxygen feed rate)×100%. The term "total oxygen consumption rate" means the sum of: (i) the oxygen consumption rate ("$R_i$") of the oxidation reaction of the PMIDA reagent to form the N-(phosphonomethyl)glycine product and formaldehyde, (ii) the oxygen consumption rate ("$R_{ii}$") of the oxidation reaction of formaldehyde to form formic acid, and (iii) the oxygen consumption rate ("$R_{iii}$") of the oxidation reaction of formic acid to form carbon dioxide and water.

In one embodiment of this invention, oxygen is fed into the reactor as described above until the bulk of PMIDA reagent has been oxidized, and then a reduced oxygen feed rate is used. This reduced feed rate preferably is used after about 75% of the PMIDA reagent has been consumed. More preferably, the reduced feed rate is used after about 80% of the PMIDA reagent has been consumed. The reduced feed rate may be achieved by purging the reactor with air, preferably at a volumetric feed rate which is no greater than the volumetric rate at which the pure molecular oxygen was fed before the air purge. The reduced oxygen feed rate preferably is maintained for from about 2 to about 40 min., more preferably from about 5 to about 20 min., and most preferably from about 5 to about 15 min. While the oxygen is being fed at the reduced rate, the temperature preferably is maintained at the same temperature or at a temperature less than the temperature at which the reaction was conducted before the air purge. Likewise, the pressure is maintained at the same or at a pressure less than the pressure at which the reaction was conducted before the air purge. Use of a reduced oxygen feed rate near the end of the PMIDA reaction tends to reduce the amount of residual formaldehyde present in the reaction solution without producing detrimental amounts of AMPA by oxidizing the N-(phosphonomethyl)glycine product.

Reduced losses of noble metal may be observed with this invention if a sacrificial reducing agent is maintained or introduced into the reaction solution. Suitable reducing agents include formaldehyde, formic acid, and acetaldehyde. Most preferably, formic acid, formaldehyde, or mixtures thereof are used. Experiments conducted in accordance with this invention indicate that if small amounts of formic acid, formaldehyde, or a combination thereof are added to the reaction solution, the catalyst will preferentially effect the oxidation of the formic acid or formaldehyde before it effects the oxidation of the PMIDA reagent, and subsequently will be more active in effecting the oxidation of formic acid and formaldehyde during the PMIDA oxidation. Preferably from about 0.01 to about 5.0 wt. % ([mass of formic acid, formaldehyde, or a combination thereof÷total reaction mass]×100%) of sacrificial reducing agent is added, more preferably from about 0.01 to about 3.0 wt. % of sacrificial reducing agent is added, and most preferably from about 0.01 to about 1.0 wt. % of sacrificial reducing agent is added.

In one preferred embodiment, unreacted formaldehyde and formic acid are recycled back into the reaction mixture for use in subsequent cycles. In this instance, the recycle stream also may be used to solubilize the PMIDA reagent in the subsequent cycles.

Typically, the concentration of N-(phosphonomethyl) glycine in the product mixture may be as great as 40% by weight, or greater. Preferably, the N-(phosphonomethyl) glycine concentration is from about 5 to about 40%, more preferably from about 8 to about 30%, and still more preferably from about 9 to about 15%. Concentrations of formaldehyde in the product mixture are typically less than about 0.5% by weight, more preferably less than about 0.3%, and still more preferably less than about 0.15%.

Following the oxidation, the catalyst preferably is subsequently separated by filtration. The N-(phosphonomethyl) glycine product may then be isolated by precipitation, for example, by evaporation of a portion of the water and cooling.

It should be recognized that the catalyst of this invention has the ability to be reused over several cycles, depending on how oxidized its surface becomes with use. Even after the catalyst becomes heavily oxidized, it may be reused by being reactivated. To reactivate a catalyst having a heavily oxidized surface, the surface preferably is first washed to remove the organics from the surface. It then preferably is reduced in the same manner that a catalyst is reduced after the noble metal is deposited onto the surface of the support, as described above.

V. EXAMPLES

The following examples are intended to further illustrate and explain the process of the present invention.

Example 1

Measuring Pore Volume of Carbon Support

A Micromeritics ASAP 2000 surface area and pore volume distribution instrument was used to acquire the data. Total surface area determination involves exposing a known weight of a solid to some definite pressure of a non-specific adsorbate gas at a constant temperature, e.g., at the temperature of liquid nitrogen, −196° C. During equilibration, gas molecules leave the bulk gas to adsorb onto the surface which causes the average number of molecules in the bulk gas to decrease which, in turn, decreases the pressure. The relative pressure at equilibrium, p, as a fraction of the saturation vapor pressure, $p_o$, of the gas is recorded. By combining this decrease in pressure with the volumes of the vessel and of the sample, the amount (i.e., the number of molecules) of gas adsorbed may be calculated by application of the ideal gas laws. These data are measured at relative pressures ($p/p_o$) of approximately 0.1 to 0.3 where the Brunauer, Emmett and Teller (BET) equation for multi-layer adsorption typically applies. With the number of adsorbed gas molecules known, it is possible to calculate the surface area using the "known" cross-sectional area of the adsorbate. For cases where only physical adsorption due to Van der Waals forces occurs (i.e., Type I Langmuir isotherms) the determination of surface area from the observed changes in pressure is accomplished using the BET equation. Pore size and pore size distributions are calculated by obtaining relative pressure data approaching $p/p_o=1$, i.e., in the regime where multi-layer adsorption and capillary condensation occur. By applying the Kelvin equation and methods developed by Barrett, Joyner and Halenda (BJH), the pore volume and area may be obtained.

Example 2

High-temperature Deoxyglenation of a Carbon Support

The high-temperature deoxygenation procedures described in the following examples may be used with any carbon support to produce a deoxygenated carbon support.

Single-Step High-TemDerature Deoxygenation #1 Using $NH_3TH_2O$ Gas

An activated carbon support (2.5 g) was placed into a 1.9 cm I.D.×40.6 cm length quartz tube. The tube was connected to a gas stream resulting from sparging a 70 to 100 ml/min. $N_2$ stream through a 70° C, 10% $NH_4OH$ aqueous solution. The quartz tube then was placed into a preheated 30.5 cm tubular furnace and pyrolyzed at 9300C for 60 min. and then cooled to room temperature under a dry $N_2$ atmosphere without contacting any air.

Single-Step High-Temperature Deoxygenation #2 Using $NH_3/H_2O$ Gas

An activated carbon support (3.55 g) was placed into a 1.9 cm I.D.×35.6 cm long quartz tube. The tube was connected to streams of 50 ml/min. of $NH_3$ gas and 89 ml/min. of steam and then placed into a preheated 30.5 cm tubular furnace and pyrolyzed at 930° C. for 30 minutes. The tube subsequently was cooled to room temperature under a dry $N_2$ atmosphere without any contact with air.

To show the advantages of deoxygenating the carbon support before dispersing the noble metal onto the surface of the support, the performances of the following two catalysts were compared: one having a carbon support, which was deoxygenated using the above treatment before platinum was dispersed onto its surface; and one having an SA-30 carbon support (Westvaco Corp. Carbon, Department Covington, Va.) which was used as received from Westvaco. Platinum.was dispersed onto the surfaces of the carbon supports using the technique described in Example 3 below. The catalysts then were reduced. In one experiment,. the catalysts were reduced using $NaBH_4$ (See Example 12 for protocol). In a second experiment, the catalysts were reduced by heating them in 20% $H_2$ and 80% argon for 8 hours at 640° C.

The reduced catalysts were used to catalyze the oxidation of PMIDA to N-(phosphonomethyl)glycine (i.e., "glyphosate") using the reaction conditions set forth in Example 5. Table 1 shows the results. Use of the deoxygenated carbon support resulted in smaller CO desorption values, less noble metal leaching, higher formaldehyde activity, and shorter reaction times.

TABLE 1

Effect of Deoxygenating the Carbon Support before Dispersing Noble Metal onto Its Surface

| Deoxygenation treatment | CO desorption from carbon support (mmole/g) | Reduction | Pt in soln. ($\mu$g/g glyph. prod.) | $CH_2O$ (mg/g glyph. prod.) | Reaction time[1] (min.) |
|---|---|---|---|---|---|
| Single-step high-temperature deoxygenation #2 | 0.23 | $NaBH_4$ Reduced (Ex. 12) | 8.6 | 28.5 | 35.1 |
| SA-30, used as received | 1.99 | same | 54.3 | 43.1 | 62.7 |
| Single-step high-temperature deoxygenation #2 | 0.23 | 8 hrs at 640° C. in 20% H2, 80% Ar | 4.8 | 15.6 | 29.8 |
| SA-30, used as received | 1.99 | same | 31 | 19.7 | 50.7 |

[1] When ≧98% of the PMIDA has been consumed.

Example 3

Depositing Platinum Onto the Surface of a Carbon Support

Twenty grams of NUCHAR activated carbon SA-30 (Westvaco Corp. Carbon, Department Covington, VA.) was slurried in 2 L of water for 2 hours. Then, 2.81 grams of $H_2PtCl_6$ dissolved in about 900 ml of water was added dropwise over a period of 3 to 4 hours. After the $H_2PtCl_6$ solution was completely added, the slurry was stirred for 90 more minutes. The pH of the slurry then was readjusted to 10.5 using NaOH, and stirred for 10 to 14 more hours. The resulting slurry was filtered and washed with water until the filtrate reached a constant conductivity. The wet cake was dried at 125° C. under vacuum for 10 to 24 hours. This material produced 5% platinum on carbon upon reduction.

It should be recognized that the above procedure may be used to deposit platinum onto the surface of other carbon supports as well.

Example 4

High-temperature Hydrogen Reduction of a Carbon Support

Approximately 5.8 g of a dried, unreduced catalyst consisting of 5% platinum on a NUCHAR SA-30 carbon support (Westvaco Corp., Carbon Department, Covington, Va.) was dehydrated in-situ at 135° C. in argon for one hour before being reduced at 640° C. with 20% $H_2$ in argon for 11 hours. Upon cooling to room temperature under 20% $H_2$ in argon, the catalyst was ready to use.

It should be recognized that the above procedure may be used to heat other carbon supports as well.

Example 5

Use of the Catalyst to Oxidize PMIDA to N-(Phosphonomethyl)glycine

This example demonstrates the use of high-temperature gas-phase reduction to improve catalyst performance.

An Aldrich catalyst consisting of 5% platinum on an activated carbon support (catalog No. 20,593-1, Aldrich Chemical Co., Inc., Milwaukee, Wis.) was heated at 640° C. for 4–6 hours in the presence of 20% $H_2$ and 80% argon. Subsequently, it was used to catalyze the oxidation of PMIDA to Glyphosate. Its performance was compared to the performance of a sample of the Aldrich catalyst which was used as received from Aldrich.

The PMIDA oxidation reaction was conducted in a 200 ml glass reactor using 11.48 g of PMIDA, 0.5% catalyst (dry basis), a total reaction mass of 140 g, a temperature of 90° C., a pressure of 50 psig, a stir rate of 900 rpm, and an oxygen flow rate of 100 ml/min.

Table 2 shows the results. The high-temperature hydrogen-reduced catalyst had less leaching, better formaldehyde activity, and produced less NMG. Also, reaction time was shortened by 30% when the high-temperature hydrogen-reduced catalyst was used.

TABLE 2

PMIDA Oxidation
Results for 5% Pt on Activated Carbon (Aldrich Cat. No. 20,593-1)

| Catalyst | As Received | High-Temp., $H_2$ Reduced |
|---|---|---|
| PMIDA (%) | 0.4619 | 0.4430 |
| N-(phosphonomethyl)glycine (%) | 5.58 | 5.54 |
| $HCO_2H$ (mg/g glyph. prod.) | 46.99 | 35.87 |
| $CH_2O$ (mg/g glyph. prod.) | 32.96 | 14.60 |
| NMG (mg/g glyph. prod.) | 3.58 | 1.32 |
| AMPA (ppm) | 172.5 | 182.0 |
| End Point (min.) | 64.67 | 44.17 |
| Pt in soln. (μg/g glyph. prod.) | 32.26 | 10.50 |
| % of Pt Lost | 0.72 | 0.232 |

Example 6

Further Examples Showing Use of Catalyst to Oxidize PMIDA to N-(Phosphonomethyl)glycine This example demonstrates using the high-temperature, gas-phase reduction treatment and ammonia washing to improve catalyst performance.

The performances of six catalysts in catalyzing the PMIDA oxidation were compared. These catalysts were: (a) a catalyst consisting of 5% platinum on an activated carbon support (Catalog No. 33,015-9, Aldrich Chemical Co., Inc., Milwaukee, Wis.); (b) the catalyst after being washed with ammonia (ammonia washing was conducted using the same technique described in Example 10 except that the pH of the catalyst slurry was adjusted to and maintained at 11.0 rather than 9.5); (c) the catalyst after being heated at 75° C. in 20% $H_2$ and 80% argon for 4–6 hours (GPR@75° C.); (d) the catalyst after being heated at 640° C. for 4–6 hours in the presence of 20% $H_2$ and 80% argon (GPR@640° C.) ; and (e) two catalysts after being washed with ammonia and then heated at 640° C. for 4–6 hours in the presence of 20% $H_2$ and 80% argon. The PMIDA oxidation reaction conditions were the same as in Example 5.

Table 3 shows the results. The untreated catalyst showed relatively high leaching and poor formaldehyde activity. High-temperature gas-phase reduction at 640° C. in the presence of $H_2$ leads to the greatest decrease in leaching and increase in formaldehyde activity. Heating the catalyst at 75° C. in 20% $H_2$ at 75° C. decreased leaching to a lesser extent, but did not enhance the formaldehyde activity.

TABLE 3

PMIDA Oxidation Results for 5% Pt on Activated Carbon (Aldrich Cat. No. 33,015-9)

| Catalyst | As-received | $NH_3$ wash w/o GPR[1] | GPR @ 75° C. | GPR @ 640° C. | $NH_3$ wash + GPR @ 640° C. | $NH_3$ wash + GPR @ 640° C. |
|---|---|---|---|---|---|---|
| PMIDA (%) | ND | ND | ND | 0.097 | 0.083 | ND |
| Glyphosate (%) | 5.87 | 5.65 | 5.81 | 5.89 | 5.85 | 5.91 |
| $HCO_2H$ (mg/g glyph. prod.) | 43.46 | 43.65 | 38.97 | 42.14 | 46.91 | 52.12 |
| $CH_2O$ (mg/g glyph. prod.) | 19.39 | 22.73 | 19.85 | 13.78 | 15.70 | 17.61 |
| NMG (mg/g glyph. prod.) | 1.27 | 0.89 | 0.89 | 1.00 | 1.31 | 1.68 |
| AMPA (ppm) | 149.4 | 147.6 | 134.6 | 349.8 | 324.8 | 283.8 |
| End Point (min.) | 39.33 | 44.33 | 38 | 31.42 | 34.33 | 33.33 |
| Pt in soln. (μg/g glyph. prod.) | 42.59 | 40.71 | 27.54 | 5.26 | 5.30 | 4.23 |
| % of Pt Lost | 1 | 0.92 | 0.64 | 0.12 | 0.12 | 0.1 |

[1]-"GPR" means reduction in $H_2$
[2]-"ND" means none detected.

In the next experiment, five catalysts were analyzed while catalyzing the PMIDA oxidation. These catalysts were: (a) a catalyst consisting of 5% platinum on NUCHAR SA-30 (Westvaco Corp., Carbon Department, Covington, Va.); (b) the catalyst after being treated with $NaBH_4$ (see Example 12 for protocol); (c) the catalyst after being heated at 75° C. in 20% $H_2$ and 80% argon for 4–6 hours (GPR@75° C.); (d) the catalyst after being heated at 640° C. in 20% $H_2$ and 80% argon for 4–6 hours (GPR@640° C.); (e) the catalyst after being washed with ammonia (using the same technique described in Example 10) and then heated at 640° C. in 20% $H_2$ and 80% argon for 4–6 hours. The reaction conditions were the same as those in Example 5.

Table 4 shows the results. The untreated catalyst showed relatively high platinum leaching and low formaldehyde activity. The catalyst also showed high leaching and low formaldehyde activity after being treated with $NaBH_4$, as did GPR@75° C. In contrast, GPR@640° C. showed a greater formaldehyde activity and less leaching.

pass energy. The X-ray source was operated at 40 watts power and data were collected from the 200 μm spot on the sample being irradiated. These conditions give high sensitivity but low energy resolution. The spectra were accumulated taking a 1.0 eV step size across the region from 1100 eV to 0 eV and co-adding repetitive scans to achieve acceptable signal/noise in the data. The elements present were identified and quantified using the standard data processing and analysis procedures provided with the instrumentation by the vendor. From the relative intensities of the photoelectron peaks, the relative atomic concentrations of the elements Pt/C/o are obtained. ESCA analysis is generally cited as having a precision of ±20% using tabulated response factors for a particular instrument configuration.

Table 5 shows the C/O and O/Pt ratios at the surface of each fresh catalyst, and the amount of leaching for each of

TABLE 4

PMIDA Oxidation Results Using 5% Pt on NUCHAR SA-30

| Catalyst | Unreduced | $NaBH_4$ red. | GPR @ 75° C. | GPR @ 640° C. | $NH_3$ wash + GPR @ 640° C. |
|---|---|---|---|---|---|
| Glyphosate (%) | 2.50 | 5.71 | 4.92 | 5.17 | 5.19 |
| $HCO_2H$ (mg/g glyph. prod.) | 59.56 | 51.14 | 57.85 | 30.85 | 38.21 |
| $CH_2O$ (mg/g glyph. prod.) | 115.28 | 43.13 | 48.52 | 19.67 | 20.79 |
| NMG (mg/g glyph. prod.) | 1.64 | 2.17 | 6.41 | 0.37 | 1.73 |
| AMPA (ppm) | 58.16 | 193.9 | 174.0 | 138.5 | 156.3 |
| End point (min.) | 62.67 | 62.67 | 70.67 | 50.67 | 59.33 |
| Pt in soln. (μg/g glyph. prod.) | 84.00 | 54.29 | 81.30 | 30.95 | 19.27 |
| % of Pt Lost | 0.84 | 1.24 | 1.6 | 0.64 | 0.4 |

Example 7

Effect of C/O and O/Pt Ratios at the Surface of the Catalyst

The carbon atom to oxygen atom ratio and the oxygen atom to platinum atom ratio at the surfaces of various fresh catalysts were analyzed using a PHI Quantum 2000 ESCA Microprobe Spectrometer (Physical Electronics, Eden Prairie, Minn.). The surface analysis was performed by electron spectroscopy for chemical analysis ("ESCA") with the instrument in a retardation mode with the analyzer at fixed band pass energy (constant resolution). The analysis entails irradiation of the sample with soft X-rays, e.g., Al $K_\alpha$ (1486.6 eV), whose energy is sufficient to ionize core and valence electrons. The ejected electrons leave the sample with a kinetic energy that equals the difference between the exciting radiation and the "binding energy" of the electron (ignoring work function effects). Because only the elastic electrons, i.e., those that have not undergone energy loss by any inelastic event, are measured in the photoelectron peak, and because the inelastic mean free path of electrons in solids is short, ESCA is inherently a surface sensitive technique. The kinetic energy of the electrons is measured using an electrostatic analyzer and the number of electrons are determined using an electron multiplier. The data are presented as the number of electrons detected versus the binding energy of the electrons. ESCA survey spectra were taken using monochromatic Al $K_\alpha$ x-rays for excitation of the photoelectrons with the analyzer set for a 117 eV band the catalysts during a single-cycle PMIDA oxidation reaction.

TABLE 5

Effects of C/O and O/Pt Ratios During PMIDA Oxidation[1]

| Catalyst | Reduction Treatment After Depositing Noble Metal | C/O Ratio | O/Pt Ratio | Pt in Soln. $(\mu g/g)^2$ | $CH_2O$ $(mg/g)^3$ |
|---|---|---|---|---|---|
| 5% Pt on deoxygenated carbon[5] | $NaBH_4$ Reduced | 23.7 | 3 | ND[4] | |
| same | Pt(II)[6] 640° C./9 hr/10% $H_2$ | 35.3 | 17 | 1.2 | 24.44 |
| same | $NaBH_4$ Reduced | 21.1 | 3 | 6.9 | |
| Aldrich Cat. No. 33015-9 | 640° C./6 hr/20% $H_2$ | 67.9 | 3 | 5.2 | 13.78 |
| same | 75° C./6 hr/20% $H_2$ | 13.4 | 10 | 27.5 | 19.85 |
| same | Used as Received | 13.3 | 10 | 42.6 | 19.39 |
| Aldrich Cat. #20593-1 | 640° C./6 hr/20% $H_2$ $NH_3$ wash/pH = 11 | 45.2 | 7 | 10.5 | 21.90 |
| same | 640° C./6 hr/20% $H_2$ | 37.7 | 10 | 10.5 | 14.60 |
| same | Used as Received | 9.1 | 26 | 32.3 | 32.96 |
| 5% Pt on SA-30 Westvaco carbon | 640° C./7 hr/20% $H_2$ $NH_3$ wash/pH = 9.5 | 67.7 | 8 | 19.3 | 20.79 |

TABLE 5-continued

Effects of C/O and O/Pt Ratios During PMIDA Oxidation[1]

| Catalyst | Reduction Treatment After Depositing Noble Metal | C/O Ratio | O/Pt Ratio | Pt in Soln. ($\mu$g/g)[2] | $CH_2O$ (mg/g)[3] |
|---|---|---|---|---|---|
| same | 640° C./8 hr/20% $H_2$ | 63.3 | 8 | 30.9 | 19.67 |
| same | 75° C./7 hr/20% $H_2$ | 13.2 | 32 | 81.3 | 48.52 |

[1] The reaction conditions were the same as those used in Example 5.
[2] $\mu$g Pt which leached into solution per gram Glyphosate produced.
[3] mg formaldehyde per gram Glyphosate produced.
[4] "ND" means none detected.
[5] The carbon support was deoxygenated using the singe-step high-temperature deoxygenation technique #2 described in Example 2.
[6] The Pt was deposited using diamminedinitrito P(II) as described in Example 11.

Example 8

Analysis of Catalyst Surface Using Thermogravimetric Analysis With In-line Mass Spectroscopy (TGA-MS)

The concentration of oxygen-containing functional groups at the surfaces of various fresh catalysts was determined by thermogravimetric analysis with in-line mass spectroscopy (TGA-MS) under helium. To perform this analysis, a dried sample (100 mg) of fresh catalyst is placed into a ceramic cup on a Mettler balance. The atmosphere surrounding the sample then is purged with helium using a flow rate 150 ml/min. at room temperature for 10 minutes. The temperature subsequently is raised at 10° C. per minute from 20 to 900° C., and then held at 900° C. for 30 minutes. The desorptions of carbon monoxide and carbon dioxide are measured by an in-line mass spectrometer. The mass spectrometer is calibrated in a separate experiment using a sample of calcium oxalate monohydrate under the same conditions.

Table 6 shows the amount of carbon monoxide desorbed per gram of each catalyst using TGA-MS, and the amount of leaching for each of the catalysts during a single-cycle PMIDA oxidation reaction using the same reaction conditions as in Example 5. As Table 6 shows, leaching tends to decrease as the amount of CO desorption decreases, and is particularly low when the desorption is no greater than 1.2 mmole/g (mmole CO desorbed per gram of catalyst).

TABLE 6

Effects of Oxygen-Containing Functional Groups Which Desorb from Catalyst Surface as CO during TGA-MS

| Catalyst | Reduction Treatment | TGA-MS (mmole/g)[1] | Pt in Soln. ($\mu$g/g)[2] | $CH_2O$ (mg/g)[3] |
|---|---|---|---|---|
| Aldrich Cat. #33015-9 | 640° C./6 hr/20% $H_2$ | 0.41 | 5.2 | 13.78 |
| same | 640° C./6 hr/20% $H_2$ $NH_3$ wash/pH = 9.5 | 0.38 | 5.3 | 15.70 |
| same | 75° C./6 hr/20% $H_2$ | 1.87 | 27.5 | 19.85 |
| same | $NH_3$ wash/pH = 9.5 | 1.59 | 40.7 | 22.73 |
| same | Used as Received | 1.84 | 42.6 | 19.39 |

[1] mmole of CO per gram of catalyst
[2] $\mu$g of noble metal which leaches into solution per gram of Glyphosate produced
[3] mg of formaldehyde per gram of Glyphosate produced

Example 9

Effect of Temperature During High-temperature Gas-phase Reduction

This example demonstrates the effects of using various temperatures when heating the catalyst in the presence of a reducing agent.

An unreduced catalyst having 5% platinum on an activated carbon support (which was deoxygenated using the single-step high-temperature deoxygenation technique #2 described in Example 2 before the platinum is deposited) was heated at various temperatures in 10% $H_2$ and 90% argon for about 2 hours. The catalyst then was used to catalyze the PMIDA oxidation reaction. The reaction was conducted in a 250 ml glass reactor using 5 g PMIDA, 0.157% catalyst (dry basis), 200 g total reaction mass, a temperature of 80° C., a pressure of 0 psig, and an oxygen flow rate of 150 ml/min.

The results are shown in Table 7. Increasing the reduction temperature from 125° C. to 600° C. reduces the amount of noble metal leaching and increases the formaldehyde oxidation activity during the oxidation reaction of PMIDA into Glyphosate.

TABLE 7

Effects of Reduction Temperature

| Reduction Temperature (° C.) | Pt in Soln. (normalized[1]) | $CH_2O$ (normalized[2]) | C/O Ratio | O/Pt Ratio |
|---|---|---|---|---|
| 125 | 1.00 | 0.41 | 26 | 13 |
| 200 | 0.44 | 0.80 | 27 | 14 |
| 400 | 0.18 | 0.93 | 42 | 10 |
| 500 | 0.14 | 0.95 | 32 | 14 |
| 600 | 0.06 | 1.00 | 40 | 11 |

[1] A normalized value of 1.00 corresponds to the highest amount of Pt observed in solution during this experiment.
[2] A normalized value of 1.00 corresponds to the highest formaldehyde activity during this experiment.

Example 10

Washing the Catalyst With Ammonia

An unreduced catalyst (6.22 g) consisting of 5% platinum on an activated carbon support (which was deoxygenated using the single-step high-temperature deoxygenation technique #2 described in Example 2 before the platinum was deposited onto the support) was slurried in 500 ml of water for 30 minutes. Afterward, the pH of the slurry was adjusted to 9.5 with diluted aqueous ammonia, and the slurry was stirred for one hour, with aqueous ammonia being periodically added to maintain the pH at 9.5. The resulting slurry was filtered and washed once with about 300 ml of water. The wet cake then was dried at 125° C. under vacuum for about 12 hours. This catalyst was heated at 640° C. for 11 hours in 10% $H_2$ and 90% argon, and then compared with two other catalysts consisting of 5% platinum on NUCHAR activated carbon: (a) one reduced at room temperature with $NaBH_4$ (see Example 12 for protocol), and (b) one heated at 640° C. in 10% $H_2$ and 90% argon for 11 hours. The reactions were the same as those in Example 5.

The results are shown in Table 8. Platinum leaching was the lowest with the catalyst which was washed with ammonia before high-temperature hydrogen reduction.

TABLE 8

Effects of Ammonia Washing

| Catalyst soln. | $CH_2O$ (mg/g)[1] | $HCO_2H$ (mg/g) | NMG (mg/g) | Pt in ($\mu$g/g) |
|---|---|---|---|---|
| $NH_3$-washed, High-Temp., $H_2$-reduced | 10.62 | 28.79 | 0.83 | 0.50 |

TABLE 8-continued

Effects of Ammonia Washing

| Catalyst soln. | CH$_2$O (mg/g)[1] | HCO$_2$H (mg/g) | NMG (mg/g) | Pt in (μg/g) |
|---|---|---|---|---|
| High-temp., H$_2$-reduced | 14.97 | 27.82 | 1.38 | 4.64 |
| Room-Temp., NaBH$_4$-reduced | 28.51 | 70.16 | 2.59 | 8.64 |

[1]These quantities are per gram Glyphosate produced.

Example 11

Use of a Less Oxidizing Noble Metal Precursor

Platinum was deposited on an activated carbon support using diamminedinitrito platinum (II). Approximately 20 g of an activated carbon support was deoxygenated using the single-step high-temperature deoxygenation technique #2 described in Example 2. Next, it was slurried in 2 L of water for 2 hours. Approximately 51.3 g of a 3.4% solution of diamminedinitrito platinum (II), diluted to 400 g with water, then was added dropwise over a period of 3–4 hours. After addition was complete, stirring was continued for 90 more minutes. The pH was re-adjusted to 10.5 by adding diluted aqueous NaOH, and stirring was conducted for 10–14 more hours. The slurry then was filtered and washed with a plentiful amount of water until the filtrate reached constant conductivity. The wet cake was dried at 125° C. under vacuum for 10–24 hours. The resulting catalyst was heated at 640° C. for 4–6 hours in 10% H$_2$ and 90% argon.

A control was prepared using H$_2$PtCl$_6$ to deposit platinum onto the same carbon. The control was heated under the same conditions as the catalyst prepared using diamminedinitrito platinum (II).

These catalysts were compared while catalyzing the PMIDA oxidation reaction. The reaction conditions were the same as those in Example 5.

The catalyst prepared using diamminedinitrito platinum (II) showed less leaching than the control. Only 1.21 μg platinum per gram of Glyphosate produced leached into solution, which was about three times better than the control.

Example 12

Reducing the Catalyst Surface Using NaBH$_4$

The purpose of this example is to demonstrate the effects of reducing the catalyst using NaBH$_4$.

Approximately 5 g of an activated carbon support (which was deoxygenated using the single-step high-temperature deoxygenation technique #2 described in Example 2 before the platinum was deposited onto the support) was slurried with 85 ml of distilled water in a 250 ml round bottom flask. The slurry was stirred in a vacuum for about 1 hour. Next, 0.706 g of H$_2$PtCl$_6$ in 28 ml of distilled water was added to the slurry at a rate of about 1 ml per 100 seconds with the vacuum still being applied. After stirring overnight in the vacuum, the reactor was brought to atmospheric pressure by admitting a flow of N$_2$. After allowing the slurry to settle, approximately 30 ml of colorless supernatant was decanted. The remaining slurry was transferred to a 100 ml Teflon round bottom. At this point, the pH was adjusted to 12.2 with 0.3 g of NaOH. Then, 2.3 ml of NaBH$_4$ in 14 M NaOH was added at 0.075 ml/min. Subsequently, the resulting slurry was stirred for one hour, filtered, and washed five times with 50 ml of distilled water. The catalyst then was dried at 125° C. and 6 mmHg for 12 hours.

The resulting catalyst was used to catalyze the PMIDA oxidation. The reaction was conducted in a 300 ml stainless steel reactor using 0.5% catalyst, 8.2% PMIDA, a total reaction mass of 180 g, a pressure of 65 psig, a temperature of 90° C., an agitation rate of 900 rpm, and an oxygen feed rate of 72 ml/min.

A control experiment also was conducted at the same reaction conditions using 5.23% platinum on an activated carbon support (which was deoxygenated using the single-step high-temperature deoxygenation technique #2 described in Example 2 before the platinum was deposited onto the support).

Table 9 shows the results using the NaBH$_4$-reduced catalyst, and Table 10 shows the results of the control experiment. Reducing with NaBH$_4$ reduced the amount of noble metal leaching. It also reduced the amount of formaldehyde and NMG after a period of use.

TABLE 9

Results Using Catalyst Treated with NaBH$_4$

| Run # | 1 | 2 | 3 | 4 | 5 | 6 |
|---|---|---|---|---|---|---|
| Glyphosate (%) | 5.79 | 5.81 | 5.75 | 5.74 | 5.79 | 5.77 |
| PMIDA (%) | 0.23 | 0.08 | 0.13 | 0.22 | 0.13 | 0.13 |
| CH$_2$O (mg/g glyph) | 28.5 | 31.5 | 47.8 | 38.8 | 41.6 | 45.8 |
| HCO$_2$H (mg/g glyph) | 70.2 | 90.5 | 100.5 | 96.6 | 98.8 | 99.0 |
| AMPA/MAMPA (%) | 0.02 | 0.01 | 0.01 | 0.01 | 0.01 | 0.01 |
| NMG (mg/g glyph) | 2.6 | 3.6 | 3.6 | 4.2 | 4.7 | 4.7 |
| Pt in Soln. (μg/g glyph.) | 8.64 | 8.60 | 5.22 | 6.96 | 6.91 | 5.20 |
| % of Pt Lost | 0.20 | 0.20 | 0.12 | 0.16 | 0.16 | 0.12 |

TABLE 10

Results Using Catalyst which was not treated with NaBH$_4$

| Run # | 1 | 2 | 3 | 4 | 5 | 6 |
|---|---|---|---|---|---|---|
| Glyphosate (%) | 5.36 | 5.63 | 5.37 | 5.50 | 5.56 | 5.59 |
| PMIDA (%) | 0.18 | 0.15 | 0.25 | 0.21 | 0.18 | 0.23 |
| CH$_2$O (%) | 20.9 | 23.6 | 38.4 | 44.2 | 47.7 | 58.3 |
| HCO$_2$H (%) | 27.8 | 63.8 | 96.5 | 98.4 | 102.2 | 102.0 |
| AMPA/MAMPA (%) | 0.04 | 0.02 | 0.04 | 0.02 | 0.02 | 0.03 |
| NMG (mg/g glyph) | 1.5 | 3.0 | 5.4 | 6.9 | 10.6 | 7.3 |
| Pt in Soln (μg/g glyph.) | 63.6 | 62.2 | 44.7 | 34.6 | 28.8 | 28.6 |
| % of Pt Lost | 1.30 | 1.34 | 0.92 | 0.73 | 0.61 | 0.61 |

Example 13

Use of Bismuth as a Promoter

A 500 g solution was prepared consisting of 10$^{-3}$ M Bi(NO$_3$)$_3$.5H$_2$O in 10$^{-3}$ M formic acid solution. This solution was added to 500 g of a 5% formaldehyde solution containing 6.0 g of 5% platinum on an activated carbon support. The solution was stirred at 40° C. under N$_2$ overnight and then filtered with a Buchner funnel. An aliquot was dried and subsequently analyzed by X-ray fluorescence. The catalyst had a loss on drying ("LODI") of 63%. The dry catalyst was found to contain approximately 3% bismuth and 4% platinum.

The following were placed into a 300 ml stainless steel autoclave: 16.4 g of PMIDA; 4.16 g of an activated carbon catalyst, 0.68 g of the above catalyst consisting of 3% bismuth /4% platinum on its surface, and 179.4 g of water.

The reaction was conducted at a pressure of 65 psig, a temperature of 90° C., an oxygen flow rate of 38 ml/min., and a stir rate of 900 rpm. The reaction was allowed to proceed until the PMIDA was depleted. The Glyphosate solution was separated from the catalyst via filtration and the solution was neutralized with 6 g of 50% NaOH solution. The catalyst was recycled with no purge through 5 runs. Analysis of the Glyphosate solution was done for each run. Two controls also were conducted in the same manner as above except that the 0.68 g of the Bi/Pt/carbon catalyst was omitted.

The results are shown in Table 11. The runs having the Bi/Pt/carbon catalyst produced lower levels of formaldehyde, formic acid, and NMG in the product.

dissolved in 75 ml of water. The solution was added dropwise to the carbon slurry. After all the solution was added, the slurry was stirred for two hours. The slurry then was filtered and washed with a plentiful amount of water until the filtrate reached a constant conductivity. The wet cake was dried at 125° C. under vacuum to give 1% iron on carbon. Following drying, the 1% iron on carbon was calcined in argon at about 500° C. for 8 hours.

To deposit platinum onto the surface of the carbon support, 2.5 g of the 1% iron on carbon first was slurried in about 180 ml of water. Then, 0.355 g of $H_2PtCl_6$ was dissolved in about 70 ml of water and added dropwise. After all the solution was added, the slurry was stirred for three

TABLE 11

| | PMIDA Oxidation Results Using Pt/Bi/C Catalyst | | | | | | |
|---|---|---|---|---|---|---|---|
| | CONTROL #1 | CONTROL #2 | 1ST RUN | 2ND RUN | 3RD RUN | 4TH RUN | 5TH RUN |
| Glyphosate (%) | 5.7 | 5.59 | 5.69 | 5.72 | 5.87 | 5.74 | 5.68 |
| PMIDA (%) | ND | ND | 0.04 | 0.07 | 0.085 | 0.04 | 0.046 |
| AMPA (%) | 0.034 | 0.031 | 0.015 | 0.009 | 0.008 | DBNQ[1] | DBNQ |
| $CH_2O$ (mg/g glyph. prod.) | 142 | 138 | 28 | 31 | 34 | 38 | 42 |
| $HCO_2H$ (mg/g glyph. prod.) | 56 | 57 | DBNQ | 7 | 14 | 17 | 23 |
| AMPA/MAMPA (%) | 0.047 | 0.041 | 0.021 | 0.014 | 0.013 | 0.014 | 0.013 |
| NMG (mg/g glyph. prod.) | 16.3 | 19.3 | 0.7 | 0.9 | 1.4 | 2.3 | 2.6 |

[1]DBNQ = detectable, but not quantitated.

Example 14

Depositing a Tin Promoter on a Carbon Support

An activated carbon (20 g) was slurried in about 2 L of water. Next, 0.39 g of $SnCl_2.2H_2O$ was dissolved in 500 g of 0.5% $HNO_3$. The solution was added dropwise to the carbon slurry. After all the solution was added, the slurry was stirred for 2 hours. The pH then was adjusted to 9.5, and the slurry was stirred for a few more hours. Next, the slurry was filtered and washed with a plentiful amount of water until the filtrate reached a constant conductivity. The wet cake was dried at 125° C. under vacuum to give 1% tin on carbon. Following drying, the 1% tin on carbon was calcined in argon at 500° C. for 6 hours.

To deposit platinum onto the carbon support, 5 g of the 1% tin on carbon first was slurried in about 500 ml of water. Then 0.705 g of $H_2PtCl_6$ was dissolved in about 125 ml of water and added dropwise. After all the $H_2PtCl_6$ solution was added, the slurry was stirred for 2.5 hours. The pH then was adjusted to 9.5 with diluted NaOH and stirring was continued for a few more hours. The slurry then was filtered and washed with a plentiful amount of water until the filtrate reached constant conductivity. The wet cake was dried at 125° C. under vacuum.

This technique produced a catalyst comprising 5% platinum and 1% tin on carbon.

Example 15

Depositing an Iron Promoter Onto a Carbon Support

Approximately 5 g of activated carbon was slurried in about 500 ml of water. Next, 0.25 g of $FeCl_3.6H_2O$ was more hours. The pH then was adjusted to about 10.0 with diluted NaOH and stirring was continued for a few more hours. Next, the slurry was filtered and washed with a plentiful amount of water until the filtrate reached a constant conductivity. The wet cake was dried at 125° C. under vacuum.

This technique produces a catalyst comprising 5% platinum and 1% iron on carbon.

Example 16

Effect of Presence of Noble Metal on the Surface of the Carbon Support

This example shows the advantages of using a carbon support having a noble metal on its surface for effecting the oxidation of PMIDA rather than a carbon-only catalyst having no noble metal on its surface.

The PMIDA oxidation reaction was conducted in the presence of a carbon-only catalyst which was deoxygenated using the single-step high-temperature deoxygenation technique #2 described in Example 2. The reaction was carried out in a 300 ml stainless steel reactor using 0.365% catalyst, 8.2% PMIDA, a total reaction mass of 200 g, a pressure of 65 psig, a temperature of 90° C., an agitation rate of 900 rpm, and an oxygen feed rate of 38 ml/min.

Table 12 shows the reaction times (i.e., the time for at least 98% of the PMIDA to be consumed) of 5 cycles for the carbon-only catalyst. Table 12 also shows the reaction times for the two Pt-on-carbon catalysts in Example 12 over 6 cycles under the reaction conditions described Example 12. As may be seen from Table 12, the deactivation of the carbon-only catalyst per cycle generally tends to be greater (i.e., the reaction times tend to increase more per cycle) than the deactivation of the carbon catalysts which had a noble metal on their surfaces. The deactivation particularly appears to be less where the catalyst has been reduced with NaBH$_4$ after the noble metal was deposited onto the surface. Without being bound by any particular theory, it is believed that the deactivation of the catalyst reduced with NaBH$_4$ was less than the deactivation of the other Pt-on-carbon catalyst because the platinum on the NaBH$_4$ catalyst leached less than the platinum on the other Pt-on-carbon catalyst. See Example 12, Tables 9 & 10.

TABLE 12

Results Using Catalyst which was not treated with NaBH$_4$

| Run # | 1 | 2 | 3 | 4 | 5 | 6 |
|---|---|---|---|---|---|---|
| Run Time for Carbon-Only Catalyst (min.) | 45.4 | 55.0 | 64.4 | 69.8 | 75.0 | |
| Run Time for 5% platinum on Carbon Catalyst which was Reduced w/ NaBH$_4$ (min.) | 35.1 | NA[1] | NA | 35.2 | 35.8 | 35.8 |
| Run Time for 5.23% platinum on Carbon Catalyst (min.) | 40.4 | 42.0 | 44.2 | 44.1 | 44.9 | 52.7 |

[1]·Not available due to temperature problems.

Example 17

The Effect of Using a Catalyst Comprising a Noble Metal Alloyed With a Promoter

This example shows the advantages of a catalyst comprising platinum alloyed with iron.

1. Catalyst Comprisin Platinum Alloyed With Iron

To prepare the catalyst comprising platinum alloyed with iron, approximately 10 grams of an activated carbon was slurried in about 180 ml of water. Next, 0.27 grams of FeCl$_3$.6H$_2$O and 1.39 grams of H$_2$PtCl$_6$ hydrate were co-dissolved in about 60 ml of water. This solution was added dropwise to the carbon slurry over a period of about 30 minutes. During the addition, the pH of the slurry dropped and was maintained at from about 4.4 to about 4.8 using a dilute NaOH solution (i.e., a 1.0 to 2.5 molar solution of NaOH). Afterward, the slurry was stirred for 30 more minutes at a pH of about 4.7. The slurry then was heated under N$_2$ to 70° C. at a rate of about 2° C./min. while maintaining the pH at about 4.7. Upon reaching 70° C., the pH was raised slowly over a period of about 30 minutes to 6.0 with addition of the dilute NaOH solution. The stirring was continued for a period of about 10 min. until the pH became steady at about 6.0. The slurry was then cooled under N$_2$ to about 35° C. Subsequently, the slurry was filtered, and the cake was washed with approximately 800 ml of water 3 times. The cake was then dried at 125° C. under a vacuum. This produced a catalyst containing 5 wt. % platinum and 0.5 wt. % iron on carbon upon heating at 690° C. in 20% H$_2$ and 80% Ar for 1–6 hr.

This catalyst was analyzed via electron microscopy, as described in more detail in Example 19. FIG. 1 is an image obtained through TEM of the carbon support. This image shows that the alloyed metal particles cwere highly dispersed and uniformly distributed throughout the carbon support (the white dots represent the metal particles; and the variations in the background intensity are believed to represent the change of the local density of the porous carbon).

Figure 2:
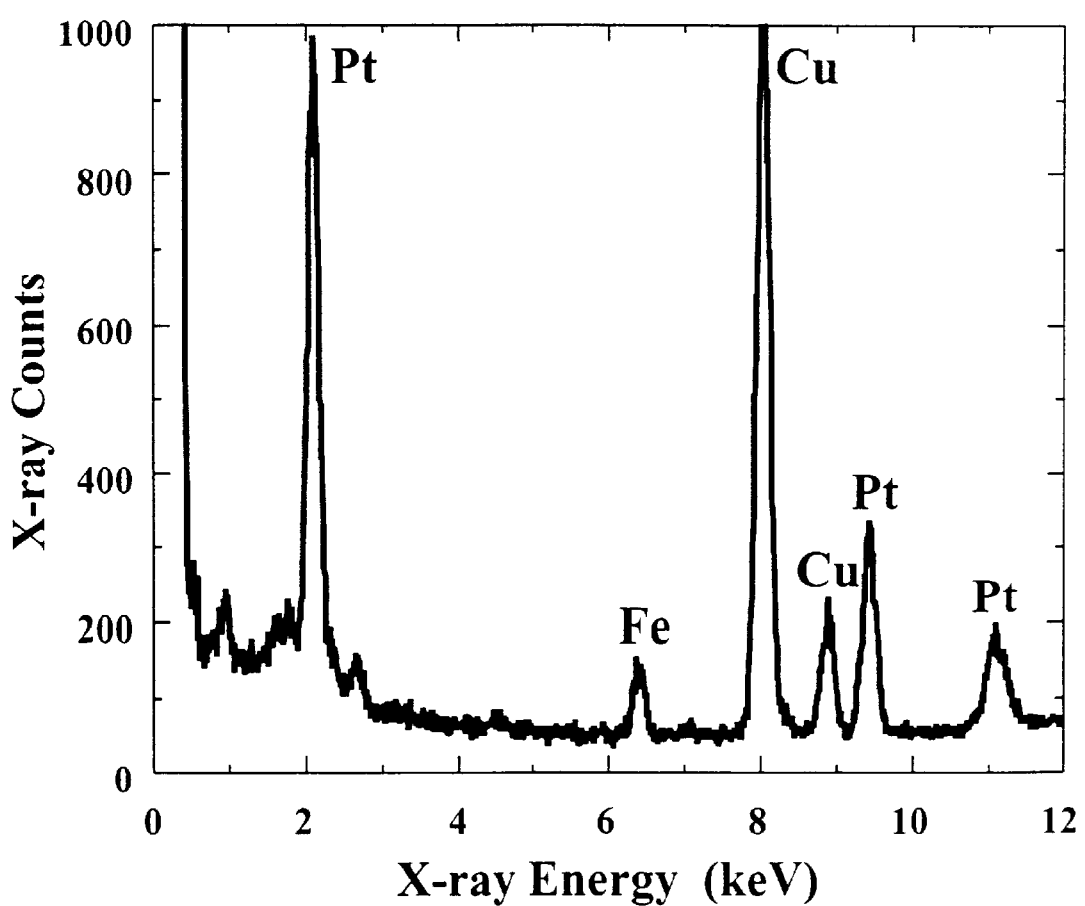
FIG. 2 is a high energy resolution X-ray spectra from an individual metal particle of an oxidation catalyst comprising a carbon support having platinum alloyed with iron at the surface of the carbon support.

The average size of the particles was about 3.5 nm, and the average distance between particles was about 20 nm. FIG. 2 is a typical high energy resolution X-ray spectra from an individual metal particle of the catalyst. As FIG. 2 shows, both platinum and iron peaks were present (the copper peaks originated from the scattering of the copper grids). Quantitative analysis of the high energy resolution X-ray spectra from different individual metal particles showed that the composition of the particles, within experimental error, did not vary with the size or the location of the metal particles on the catalyst surface.

2. Catalyst in Which Platinum was Less Alloyed With Iron

To prepare the Pt/Fe/C catalyst in which the platinum was less alloyed with iron (i.e., this catalyst has less platinum alloyed with iron than does the first catalyst described in this example), the platinum and iron were deposited sequentially onto the surface of the carbon support. Approximately 5 grams of an activated carbon was slurried in about 500 ml of water. The pH was adjusted to about 5.0 with iN HCl. Next, about 0.25 grams of FeCl$_3$.6H$_2$O was dissolved in 75 ml of water. This solution was added dropwise to the carbon slurry over a period of about 60 min. After all the solution was added, the slurry was stirred for about 2 hours. The pH was adjusted to 9.5 with the dilute NaOH solution, and the slurry was stirred for a few more hours. Afterward, the slurry was filtered and washed with a plentiful amount of water. The wet cake was dried at 125° C. under vacuum to produce 1 wt. % iron on carbon. Following drying, this 1 wt. % iron on carbon was reduced with an atmosphere containing 20% H$_2$ and 80% Ar at 635° C. for 1–6 hr. About 2.5 grams of this 1 wt. % iron on carbon was slurried in 250 ml of water. Next, about 0.36 grams of H$_2$PtCl$_6$ hydrate was dissolved in 65 ml of water, which, in turn, was added dropwise to the slurry over a period of about 60 min. After all the solution was added, the slurry was stirred for 2 hours. The slurry then was filtered and washed with a plentiful amount of water. The cake was then re-slurried in 450 ml of water. After adjusting the pH of the slurry to 9.5 with the dilute NaOH solution, the slurry was stirred for about 45 min. Next, the slurry was filtered and washed once with 450 ml of water. The wet cake was the dried at 125° C. under vacuum. This produced a catalyst containing 5 wt. % platinum and 1 wt. % iron on carbon upon reduction by heating to a temperature of 660° C. in an atmosphere containing 20% H$_2$ and 80% Ar for 1–6 hr.

3. Comparison of the Two Catalysts

These two catalysts were compared while catalyzing the PMIDA oxidation reaction. The reaction conditions were the same as those in Example 5. Table 13 shows the results. The first catalyst described in this example (i.e., the catalyst comprising a greater amount of platinum alloyed with iron) had greater stability with respect to CH$_2$O & HCO$_2$H activities; the second catalyst described in this example (i.e., the catalyst comprising a lower amount of platinum alloyed with iron) deactivated rapidly. In addition, the first catalyst retained almost half of its iron content over 25 cycles, while the second catalyst lost most of its iron in the first cycle.

TABLE 13

Comparison of Catalyst Having Pt/Fe Alloy with Catalyst Having Less Pt/Fe Alloy

| | cycle 1 | cycle 2 | cycle 3 | cycle 4 | cycle 5 | cycle 6 | cycle 7 | cycle 8 | cycle 9 | cycle 10 | cycle 11 | cycle 12 | cycle 13 |
|---|---|---|---|---|---|---|---|---|---|---|---|---|---|
| Alloyed Pt & Fe | | | | | | | | | | | | | |
| $CH_2O$ (mg/g glyph. prod.) | 10.49 | | 9.23 | | 6.04 | | 4.92 | | 4.44 | | 5.08 | | 5.24 |
| $HCO_2H$ (mg/g glyph. prod.) | 19.91 | | 29.64 | | 27.84 | | 25.62 | | 27.99 | | 29.73 | | 28.95 |
| NMG (mg/g glyph. prod.) | 0.22 | | 0.44 | | 0.28 | | 0 | | 0 | | 0 | | 0 |
| Pt in soln. (µg/g glyph. prod.) | 5.08 | | 4.87 | | 3.6 | | 3.06 | | | | | | |
| % of Fe Lost | 44 | | 1.9 | | 1.2 | | 0.8 | | | | | | |
| Less alloyed Pt & Fe | | | | | | | | | | | | | |
| $CH_2O$ (mg/g glyph. prod.) | 10.16 | 10.7 | 12.24 | 13.56 | 14.68 | | | | | | | | |
| $HCO_2H$ (mg/g glyph. prod.) | 27.23 | 37.72 | 45.01 | 54.57 | 61.14 | | | | | | | | |
| NMG (mg/g glyph. prod.) | 0 | 0.98 | 1.23 | 1.77 | 2 | | | | | | | | |
| Pt in soln. (µg/g glyph. prod.) | 3.83 | 3.36 | 3.54 | 3.44 | 3.32 | | | | | | | | |
| % of Fe Lost | 86 | 3.2 | 1.4 | 1.8 | 1.4 | | | | | | | | |

Example 18

Preparation of a Pt/Fe/Sn on Carbon Catalyst

Approximately 10 grams of an activated carbon was slurried in about 90 ml of water. Next, about 0.2 g of $SnCl_2 \cdot 2H_2O$ was dissolved in 250 ml of 0.025 M HCl. The solution was added dropwise to the carbon slurry. After all the solution was added, the slurry was stirred for 3 hr. The pH then was slowly adjusted to 9.0 with a diluted NaOH solution (i.e., a 1.0 to 2.5 molar solution of NaOH), and the slurry was stirred for a few more hours. Next, the slurry was filtered and washed with a plentiful amount of water until the filtrate reached a constant conductivity. The wet cake was dried at 125° C. under vacuum. This produced 0.9 wt. % tin on carbon. About 6 grams of this 0.9 wt. % tin on carbon was slurried in about 500 ml of water. Then approximately 0.23 grams of $Fe(NO_3)_3 \cdot 9H_2O$ and 0.85 grams of $H_2PtCl_6$ were co-dissolved in about 150 ml of water and added dropwise to the slurry. After all the solution was added, the slurry was stirred for 4 hours, and then filtered to remove excess iron (~80 wt. %). The wet cake was re-slurried in 480 ml of water. After the pH of the slurry was adjusted to 9–10 with the dilute NaOH solution, the slurry was stirred for a few more hours. Next, the slurry was filtered and washed with a plentiful amount of water until the filtrate reached a constant conductivity. The wet cake was dried at 125° C. under vacuum. This produced a catalyst containing 4.9 wt. % Pt, 0.9 wt. % tin and 0.1 wt. % iron on carbon upon high-temperature reduction by heating at 700–750° C. in 20% $H_2$ and 80% Ar for 1–6 hr.

Example 19

Electron Microscopy Characterization of Catalysts

Electron microscopy techniques were used to analyze the size, spacial distribution, and composition of the metal particles of catalysts prepared in Example 17. Before analyzing the catalyst, the catalyst was first embedded in an EM Bed 812 resin (Electron Microscopy Sciences, Fort Washington, Pa.). The resin was then polymerized at about 60° C. for approximately 24 hr. The resulting cured block was ultramicrotomed into slices having a thickness of about 50 nm. These slices were then transferred to 200 mesh copper grids for electron microscopy observation.

High-resolution analytical electron microscopy experiments were carried out in a Vacuum Generators dedicated scanning transmission electron microscope (model no. VG HB501, Vacuum Generators, East Brinstead, Sussex, England) with an image resolution of less than 0.3 nm. The microscope was operated at 100 kV. The vacuum in the specimen chamber area was below about $10^{-6}$ Pa. A digital image acquisition system (ES Vision Data Acquisition System, EmiSpec Sys., Inc., Tempe, Ariz.) was used to obtain high-resolution electron microscopy images. A windowless energy dispersive X-ray spectrometer (Link LZ-5 EDS Windowless Detector, Model E5863, High Wycombe, Bucks, England) was used to acquire high energy resolution X-ray spectra from individual metal particles. Because of its high atomic-number sensitivity, high-angle annular dark-field (HAADF) microscopy was used to observe the metal particles. An electron probe size of less than about 0.5 nm was used to obtain the HAADF images, and a probe sizeof less-than about 1 nm was used to obtain high energy resolution X-ray spectra.

The present invention is not limited to the above embodiments and can be variously modified. The above description of the preferred embodiment is intended only to acquaint others skilled in the art with the invention, its principles, and its practical application so that others skilled in the art may adapt and apply the invention in its numerous forms, as may be best suited to the requirements of a particular use.

We claim:

1. A process for the preparation of a salt of N-(phosphonomethyl)glycine, the process comprising contacting a salt of N-(phosphonomethyl)iminodiacetic acid with an oxidation catalyst in a solution or slurry having a pH less than 7 and in the presence of oxygen, wherein:

the catalyst comprises a carbon support having a noble metal and at least one promoter at a surface of the carbon support;

the noble metal is selected from the group consisting of platinum, palladium, ruthenium, rhodium, iridium, silver, osmium, gold and combinations thereof; and the promoter is selected from the group consisting of tin, bismuth, lead, cadmium, magnesium, manganese, nickel, aluminum, cobalt, titanium, antimony, selenium, iron, rhenium, cerium, zinc, and zirconium.

2. The process of claim 1 wherein the promoter is more easily oxidized than the noble metal.

3. The process of claim 1 wherein the promoter comprises bismuth.

4. The process of claim 1 wherein the promoter comprises lead.

5. The process of claim 1 wherein the promoter comprises tin.

6. The process of claim 1 wherein the promoter comprises iron.

7. The process of claim 1 wherein the promoter comprises manganese.

8. The process of claim 1 wherein the promoter comprises titanium.

9. The process of claim 1 wherein the noble metal constitutes from about 0.5 to about 20% by weight of the catalyst.

10. The process of claim 1 wherein the noble metal constitutes from about 2.5 to about 10% by weight of the catalyst.

11. The process of claim 1 wherein the noble metal constitutes no greater than about 7.5% by weight of the catalyst.

12. The process of claim 1 wherein the noble metal constitutes from about 3 to about 7.5% by weight of the catalyst.

13. The process of claim 1 wherein the promoter constitutes at least 0.05% by weight of the catalyst.

14. The process of claim 1 wherein the promoter constitutes from about 0.05 to about 10% by weight of the catalyst.

15. The process of claim 1 wherein the promoter constitutes from about 0.1 to about 10% by weight of the catalyst.

16. The process of claim 1 wherein the promoter constitutes from about 0.1 to about 2% by weight of the catalyst.

17. The process of claim 1 wherein the promoter constitutes from about 0.2 to about 1.5% by weight of the catalyst.

18. The process of claim 1 wherein the catalyst comprises two promoters at the surface of the carbon support, each said promoter constituting at least 0.05% by weight of the catalyst.

19. The process of claim 18 wherein the promoters comprise iron and tin.

20. The process of claim 1 wherein the molar ratio of noble metal to promoter is from about 10:1 to about 0.05:1.

21. The process of claim 1 wherein the catalyst comprises platinum at the surface of the carbon support.

22. The process of claim 21 wherein the carbon support is activated carbon.

23. The process of claim 22 wherein the promoter comprises bismuth.

24. The process of claim 22 wherein the promoter comprises lead.

25. The process of claim 22 wherein the promoter comprises tin.

26. The process of claim 22 wherein the promoter comprises iron.

27. The process of claim 22 wherein the promoter comprises manganese.

28. The process of claim 22 wherein the promoter comprises titanium.

29. The process of claim 22 wherein platinum constitutes from about 3 to about 7.5% by weight of the catalyst.

30. The process of claim 22 wherein the promoter constitutes from about 0.1 to about 2% by weight of the catalyst.

31. The process of claim 1 wherein the carbon support has a specific surface area of from about 10 to about 3000 m$^2$/g, as measured by the Brunauer-Emmett-Teller method.

32. The process of claim 1 wherein noble metal atoms at the surface are alloyed with the promoter.

33. The process of claim 1 wherein a majority of the noble metal atoms at the surface are alloyed with the promoter.

34. The process of claim 1 wherein substantially all of the noble metal atoms at the surface are alloyed with the promoter.

35. The process of claim 1 wherein the catalyst is characterized as yielding less than 1.2 mmole of carbon monoxide per gram of catalyst when a dry sample of the catalyst, after being heated at a temperature of about 500° C. for about 1 hour in a hydrogen atmosphere and before being exposed to an oxidant following the heating in the hydrogen atmosphere, is heated in a helium atmosphere from about 20 to about 900° C. at a rate of about 10° C. per minute, and then at about 900° C. for about 30 minutes.

36. The process of claim 35 wherein said carbon monoxide yield is no greater than about 0.7 mmole of carbon monoxide per gram of catalyst.

37. The process of claim 35 wherein said carbon monoxide yield is no greater than about 0.5 mmole of carbon monoxide per gram of catalyst.

38. The process of claim 35 wherein said carbon monoxide yield is no greater than about 0.3 mmole of carbon monoxide per gram of catalyst.

39. The process of claim 1 wherein the catalyst comprises carbon and oxygen at a surface of the carbon support and the catalyst is characterized as having a ratio of carbon atoms to oxygen atoms of at least about 20:1 at the surface as measured by x-ray photoelectron spectroscopy after the catalyst is heated at a temperature of about 500° C. for about 1 hour in a hydrogen atmosphere and before the catalyst is exposed to an oxidant following the heating in the hydrogen atmosphere.

40. The process of claim 39 wherein said ratio of carbon atoms to oxygen atoms is at least about 30:1.

41. The process of claim 39 wherein said ratio of carbon atoms to oxygen atoms is at least about 40:1.

42. The process of claim 39 wherein said ratio of carbon atoms to oxygen atoms is at least about 50:1.

43. The process of claim 39 wherein said ratio of carbon atoms to oxygen atoms is at least about 60:1.

44. The process of claim 39 wherein the catalyst is further characterized as having a ratio of oxygen atoms to noble metal atoms at the surface which is less than 8:1 as measured by x-ray photoelectron spectroscopy after the catalyst is heated at a temperature of about 500° C. for about 1 hour in a hydrogen atmosphere and before the catalyst is exposed to an oxidant following the heating in the hydrogen atmosphere.

45. The process of claim 1 wherein the process is conducted in a continuous reactor system.

46. The process of claim 1 wherein the contacting is carried out at a pressure of from about 30 to about 500 psig.

47. The process of claim 1 wherein the contacting is carried out at a pressure of from about 30 to about 130 psig.

48. The process of claim 1 wherein the contacting is carried out at a temperature of from about 20 to about 180° C.

49. The process of claim 1 wherein the contacting is carried out at a temperature of from about 50 to about 140° C.

50. The process of claim 1 wherein the contacting is carried out at a temperature of from about 80 to about 110° C.

51. The process of claim 1 wherein the contacting is carried out in a solution or slurry having a pH less than 3.

52. The process of claim 51 wherein the contacting is carried out in a solution or slurry having a pH of from about 1 to about 2.

53. A process for the preparation of N-(phosphonomethyl) glycine, the process comprising contacting N-(phosphonomethyl)iminodiacetic acid with an oxidation catalyst in a solution or slurry having a pH less than 7 and in the presence of oxygen, wherein:

the catalyst comprises a carbon support having a noble metal and at least one promoter at a surface of the carbon support;

the noble metal is selected from the group consisting of platinum, palladium, ruthenium, rhodium, iridium, silver, osmium, gold and combinations thereof; and the promoter is selected from the group consisting of tin, bismuth, lead, cadmium, magnesium, manganese, nickel, aluminum, cobalt, titanium, antimony, selenium, iron, rhenium, cerium, zinc, and zirconium.

54. The process of claim 53 wherein the contacting is carried out in a solution or slurry having a pH less than 3.

55. The process of claim 54 wherein the contacting is carried out in a solution or slurry having a pH of from about 1 to about 2.

56. The process of claim 53 wherein the promoter is more easily oxidized than the noble metal.

57. The process of claim 53 wherein the promoter comprises bismuth.

58. The process of claim 53 wherein the promoter comprises lead.

59. The process of claim 53 wherein the promoter comprises tin.

60. The process of claim 53 wherein the promoter comprises iron.

61. The process of claim 53 wherein the promoter comprises manganese.

62. The process of claim 53 wherein the promoter comprises titanium.

63. The process of claim 53 wherein the noble metal constitutes from about 0.5 to about 20% by weight of the catalyst.

64. The process of claim 53 wherein the noble metal constitutes from about 2.5 to about 10% by weight of the catalyst.

65. The process of claim 53 wherein the noble metal constitutes no greater than about 7.5% by weight of the catalyst.

66. The process of claim 53 wherein the noble metal constitutes from about 3 to about 7.5% by weight of the catalyst.

67. The process of claim 53 wherein the promoter constitutes at least 0.05% by weight of the catalyst.

68. The process of claim 53 wherein the promoter constitutes from about 0.05 to about 10% by weight of the catalyst.

69. The process of claim 53 wherein the promoter constitutes from about 0.1 to about 10% by weight of the catalyst.

70. The process of claim 53 wherein the promoter constitutes from about 0.1 to about 2% by weight of the catalyst.

71. The process of claim 53 wherein the promoter constitutes from about 0.2 to about 1.5% by weight of the catalyst.

72. The process of claim 53 wherein the catalyst comprises two promoters at the surface of the carbon support, each said promoter constituting at least 0.05% by weight of the catalyst.

73. The process of claim 72 wherein the promoters comprise iron and tin.

74. The process of claim 53 wherein the molar ratio of noble metal to promoter is from about 10:1 to about 0.05:1.

75. The process of claim 53 wherein the catalyst comprises platinum at the surface of the carbon support.

76. The process of claim 75 wherein the carbon support is activated carbon.

77. The process of claim 76 wherein the promoter comprises bismuth.

78. The process of claim 76 wherein the promoter comprises lead.

79. The process of claim 76 wherein the promoter comprises tin.

80. The process of claim 76 wherein the promoter comprises iron.

81. The process of claim 76 wherein the promoter comprises manganese.

82. The process of claim 76 wherein the promoter comprises titanium.

83. The process of claim 76 wherein platinum constitutes from about 3 to about 7.5% by weight of the catalyst.

84. The process of claim 76 wherein the promoter constitutes from about 0.1 to about 2% by weight of the catalyst.

85. The process of claim 53 wherein the carbon support has a specific surface area of from about 10 to about 3000 $m^2/g$, as measured by the Brunauer-Emmett-Teller method.

86. The process of claim 53 wherein noble metal atoms at the surface are alloyed with the promoter.

87. The process of claim 53 wherein a majority of the noble metal atoms at the surface are alloyed with the promoter.

88. The process of claim 53 wherein substantially all of the noble metal atoms at the surface are alloyed with the promoter.

89. The process of claim 53 wherein the catalyst is characterized as yielding less than 1.2 mmole of carbon monoxide per gram of catalyst when a dry sample of the catalyst, after being heated at a temperature of about 500° C. for about 1 hour in a hydrogen atmosphere and before being exposed to an oxidant following the heating in the hydrogen atmosphere, is heated in a helium atmosphere from about 20 to about 900° C. at a rate of about 10° C. per minute, and then at about 900° C. for about 30 minutes.

90. The process of claim 89 wherein said carbon monoxide yield is no greater than about 0.7 mmole of carbon monoxide per gram of catalyst.

91. The process of claim 89 wherein said carbon monoxide yield is no greater than about 0.5 mmole of carbon monoxide per gram of catalyst.

92. The process of claim 89 wherein said carbon monoxide yield is no greater than about 0.3 mmole of carbon monoxide per gram of catalyst.

93. The process of claim 53 wherein the catalyst comprises carbon and oxygen at a surface of the carbon support and the catalyst is characterized as having a ratio of carbon atoms to oxygen atoms of at least about 20:1 at the surface as measured by x-ray photoelectron spectroscopy after the catalyst is heated at a temperature of about 500° C. for about 1 hour in a hydrogen atmosphere and before the catalyst is exposed to an oxidant following the heating in the hydrogen atmosphere.

94. The process of claim 93 wherein said ratio of carbon atoms to oxygen atoms is at least about 30:1.

95. The process of claim 93 wherein said ratio of carbon atoms to oxygen atoms is at least about 40:1.

96. The process of claim 93 wherein said ratio of carbon atoms to oxygen atoms is at least about 50:1.

97. The process of claim 93 wherein said ratio of carbon atoms to oxygen atoms is at least about 60:1.

98. The process of claim 93 wherein the catalyst is further characterized as having a ratio of oxygen atoms to noble metal atoms at the surface which is less than 8:1 as measured by x-ray photoelectron spectroscopy after the catalyst is heated at a temperature of about 500° C. for about 1 hour in a hydrogen atmosphere and before the catalyst is exposed to an oxidant following the heating in the hydrogen atmosphere.

99. The process of claim 53 wherein the process is conducted in a continuous reactor system.

100. The process of claim 53 wherein the contacting is carried out at a pressure of from about 30 to about 500 psig.

101. The process of claim 53 wherein the contacting is carried out at a pressure of from about 30 to about 130 psig.

102. The process of claim 53 wherein the contacting is carried out at a temperature of from about 20 to about 180° C.

103. The process of claim 53 wherein the contacting is carried out at a temperature of from about 50 to about 140° C.

104. The process of claim 53 wherein the contacting is carried out at a temperature of from about 80 to about 110° C.

* * * * *